(12) United States Patent
Reddy et al.

(10) Patent No.: US 7,614,812 B2
(45) Date of Patent: Nov. 10, 2009

(54) WIPER WITH ENCAPSULATED AGENT

(75) Inventors: Kiran K. Reddy, Roswell, GA (US); Ning Yang, Alpharetta, GA (US); John Richard Skerrett, Alpharetta, GA (US); Guy William Provenzano, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 441 days.

(21) Appl. No.: 11/238,923

(22) Filed: Sep. 29, 2005

(65) Prior Publication Data

US 2007/0071537 A1 Mar. 29, 2007

(51) Int. Cl.
*B43K 5/14* (2006.01)
(52) U.S. Cl. ..................... 401/133; 401/132
(58) Field of Classification Search ......... 401/132–135, 401/196, 201
See application file for complete search history.

(56) References Cited

U.S. PATENT DOCUMENTS

| | | |
|---|---|---|
| 32,713 A | 7/1861 | Rand |
| 1,985,424 A | 12/1934 | Piggott |
| 2,209,914 A * | 7/1940 | Wiesendanger, Jr. et al. ............ 401/132 |
| 2,438,091 A | 3/1948 | Lynch |
| 2,528,378 A | 10/1950 | Mannheimer |
| 2,658,072 A | 11/1953 | Kosmin |
| 2,703,798 A | 3/1955 | Schwartz |
| 2,799,897 A | 7/1957 | Jansen |
| 2,831,854 A | 4/1958 | Tucker et al. |
| 2,965,576 A | 12/1960 | Wilson |
| 3,310,612 A | 3/1967 | Somerville, Jr. |
| 3,338,992 A | 8/1967 | Kinney |
| 3,341,394 A | 9/1967 | Kinney |
| 3,389,194 A | 6/1968 | Somerville |
| 3,516,941 A | 6/1970 | Matson |
| 3,542,615 A | 11/1970 | Dobo et al. |
| 3,623,659 A | 11/1971 | Malerson et al. |
| 3,692,618 A | 9/1972 | Dorschner et al. |
| 3,802,817 A | 4/1974 | Matsuki et al. |
| 3,882,035 A | 5/1975 | Loffelman et al. |
| 3,929,678 A | 12/1975 | Laughlin et al. |
| 3,943,063 A | 3/1976 | Morishita et al. |
| 3,963,699 A | 6/1976 | Rizzi et al. |
| 4,005,195 A | 1/1977 | Jandacek |
| 4,005,196 A | 1/1977 | Jandacek et al. |

(Continued)

FOREIGN PATENT DOCUMENTS

EP 0351907 A2 1/1990

(Continued)

OTHER PUBLICATIONS

*McCutcheon's*, Emulsifiers & Detergents, North American Edition, 1986, pp. 317-319.

*Primary Examiner*—David J Walczak
(74) *Attorney, Agent, or Firm*—Nathan P. Hendon; Ralph H. Dean, Jr.

(57) ABSTRACT

A substantially dry wiper having first and second substrate webs joined together in a face-to-face configuration with at least one primary capsule between the two substrate webs is disclosed. The primary capsule encapsulates a primary agent that is released from the capsule upon the occurrence of a primary triggering event. A method for using such a wiper to clean a surface is also disclosed.

20 Claims, 3 Drawing Sheets

U.S. PATENT DOCUMENTS

| | | | |
|---|---|---|---|
| 4,056,478 | A | 11/1977 | Capelli |
| 4,100,324 | A | 7/1978 | Anderson et al. |
| 4,186,743 | A | 2/1980 | Steiger |
| 4,259,383 | A | 3/1981 | Eggensperger et al. |
| 4,340,563 | A | 7/1982 | Appel et al. |
| 4,487,801 | A | 12/1984 | Turnbull et al. |
| 4,514,461 | A | 4/1985 | Woo |
| 4,515,703 | A | 5/1985 | Maq |
| 4,517,360 | A | 5/1985 | Volpenhein |
| 4,518,772 | A | 5/1985 | Volpenhein |
| 4,557,853 | A | 12/1985 | Collins |
| 4,596,481 | A * | 6/1986 | Tanaka .................. 401/132 |
| 4,597,960 | A | 7/1986 | Cohen |
| 4,600,620 | A | 7/1986 | Lloyd et al. |
| 4,604,313 | A | 8/1986 | McFarland et al. |
| 4,661,388 | A | 4/1987 | Charbonneau |
| 4,752,496 | A | 6/1988 | Fellows et al. |
| 4,777,089 | A | 10/1988 | Takizawa et al. |
| 4,797,300 | A | 1/1989 | Jandacek et al. |
| 4,818,464 | A | 4/1989 | Lau |
| 4,820,435 | A * | 4/1989 | Zafiroglu .................. 510/406 |
| 4,820,577 | A | 4/1989 | Morman et al. |
| 4,849,265 | A | 7/1989 | Ueda et al. |
| 4,878,775 | A * | 11/1989 | Norbury et al. ............. 401/132 |
| 4,898,633 | A | 2/1990 | Doree et al. |
| 4,898,781 | A | 2/1990 | Onouchi et al. |
| 4,904,524 | A | 2/1990 | Yoh |
| 4,908,233 | A | 3/1990 | Takizawa et al. |
| 4,908,252 | A | 3/1990 | Carnahan et al. |
| 4,937,370 | A | 6/1990 | Sabatelli |
| 4,950,526 | A | 8/1990 | Singleton |
| 4,976,953 | A | 12/1990 | Orr et al. |
| 4,978,483 | A | 12/1990 | Redding, Jr. |
| 4,985,459 | A | 1/1991 | Sunshine et al. |
| 4,987,632 | A | 1/1991 | Rowe et al. |
| 4,990,392 | A | 2/1991 | Groshens et al. |
| 4,999,186 | A | 3/1991 | Sabatelli et al. |
| 5,024,852 | A * | 6/1991 | Busnel et al. .................. 427/2.3 |
| 5,064,650 | A | 11/1991 | Lew |
| 5,069,897 | A | 12/1991 | Orr |
| 5,073,371 | A | 12/1991 | Turner et al. |
| 5,073,372 | A | 12/1991 | Turner et al. |
| 5,087,445 | A | 2/1992 | Haffey et al. |
| 5,090,832 | A * | 2/1992 | Rivera et al. .................. 401/132 |
| 5,126,070 | A * | 6/1992 | Leifheit et al. ......... 252/186.36 |
| 5,180,637 | A | 1/1993 | Sumii |
| 5,230,958 | A | 7/1993 | Dabi |
| 5,284,703 | A | 2/1994 | Everhart et al. |
| 5,306,515 | A | 4/1994 | Letton et al. |
| 5,306,516 | A | 4/1994 | Letton et al. |
| 5,330,835 | A | 7/1994 | Kikuchi et al. |
| 5,350,624 | A | 9/1994 | Georger et al. |
| 5,364,617 | A | 11/1994 | Bush et al. |
| 5,385,737 | A | 1/1995 | Shigeno et al. |
| 5,389,202 | A | 2/1995 | Everhart et al. |
| 5,419,958 | A | 5/1995 | Charbonneau |
| 5,462,963 | A | 10/1995 | Bush et al. |
| 5,487,884 | A | 1/1996 | Bissett et al. |
| 5,686,082 | A | 11/1997 | N'Guyen |
| 5,686,367 | A | 11/1997 | Hayashi |
| 5,792,223 | A | 8/1998 | Rivas et al. |
| 5,837,274 | A | 11/1998 | Shick et al. |
| 5,854,147 | A | 12/1998 | Nohr et al. |
| 6,060,152 | A | 5/2000 | Murchie |
| 6,068,834 | A | 5/2000 | Kvalnes et al. |
| 6,093,411 | A | 7/2000 | Bissett |
| 6,096,699 | A | 8/2000 | Bergemann et al. |
| 6,103,061 | A | 8/2000 | Anderson et al. |
| 6,121,165 | A | 9/2000 | Mackey et al. |
| 6,149,767 | A | 11/2000 | Hermans et al. |
| 6,167,890 | B1 * | 1/2001 | Gueret .................. 132/200 |
| 6,177,370 | B1 | 1/2001 | Skoog et al. |
| 6,228,385 | B1 | 5/2001 | Shick |
| 6,238,616 | B1 | 5/2001 | Ishikawa et al. |
| 6,238,678 | B1 | 5/2001 | Oblong |
| 6,268,327 | B1 | 7/2001 | Lu et al. |
| 6,270,878 | B1 | 8/2001 | Wegele et al. |
| 6,294,186 | B1 | 9/2001 | Beerse et al. |
| 6,331,230 | B1 | 12/2001 | Hermans et al. |
| 6,432,429 | B1 | 8/2002 | Maddern et al. |
| 6,440,437 | B1 | 8/2002 | Krzysik et al. |
| 6,508,604 | B1 * | 1/2003 | Bechmann et al. ......... 401/132 |
| 6,649,547 | B1 | 11/2003 | Arnold et al. |
| 6,692,825 | B2 | 2/2004 | Qin et al. |
| 6,734,157 | B2 | 5/2004 | Radwanski et al. |
| 6,736,916 | B2 | 5/2004 | Steinke et al. |
| 6,750,165 | B2 | 6/2004 | Kakiuchi et al. |
| 6,777,056 | B1 | 8/2004 | Boggs et al. |
| 6,784,126 | B2 | 8/2004 | Everhart et al. |
| 6,797,360 | B2 | 9/2004 | Varona |
| 6,797,377 | B1 | 9/2004 | DeLucia et al. |
| 6,806,213 | B2 | 10/2004 | Brooks |
| 6,831,051 | B2 | 12/2004 | Sommerville-Roberts |
| 2002/0039867 | A1 | 4/2002 | Curro et al. |
| 2002/0061954 | A1 | 5/2002 | Davis et al. |
| 2002/0192268 | A1 | 12/2002 | Alwattari et al. |
| 2003/0084914 | A1 | 5/2003 | Simon |
| 2003/0118779 | A1 | 6/2003 | Fish et al. |
| 2003/0232730 | A1 | 12/2003 | Holland et al. |
| 2004/0142828 | A1 | 7/2004 | Popplewell et al. |
| 2004/0169299 | A1 | 9/2004 | Davis et al. |
| 2004/0228811 | A1 | 11/2004 | Krzysik |
| 2004/0234711 | A1 | 11/2004 | Young |
| 2005/0067726 | A1 | 3/2005 | Yan et al. |
| 2006/0147250 | A1 * | 7/2006 | Tereschouk ................. 401/133 |
| 2006/0276356 | A1 * | 12/2006 | Panandiker et al. ......... 510/100 |

FOREIGN PATENT DOCUMENTS

| | | |
|---|---|---|
| EP | 0370600 A1 | 5/1990 |
| EP | 1421872 A2 | 5/2004 |
| GB | 802035 | 9/1958 |
| GB | 2233886 | 1/1991 |
| JP | 52-52880 | 4/1977 |
| WO | WO 01/03538 | 1/2001 |

* cited by examiner

WIPER WITH ENCAPSULATED AGENT

BACKGROUND

Wipers are commonly used articles for cleaning surfaces, personal hygiene, and absorbing liquids, greases, oils or other similar substances. Such wipers are generally produced in a myriad of well known ways. Wipers can be made by woven, knitted, wet-formed, dry-formed, and nonwoven manufacturing processes to name only a few. Materials such as cellulose and other natural fibers in addition to polymeric and other synthetic substances are often used individually or in combination to produce most common wipers.

Some such wipers have the additional utility of substances added to the wiper. Wipers are available with disinfectants, sanitizers, cleaning solutions, soaps, medicines, emollients, beauty aids, fragrances, and other such substances. Many of such wipers are delivered to the user in a wet form where the substance is saturated into the wiper or is applied to the surface of the wiper in a wet form. An example of such a wiper can be found in U.S. Pat. No. 4,904,524 to Yoh. Another common example are cleansing wet wipes which are often dispensed from a sealable, moisture-proof package or tub, or in a single wipe foil-lined pouch. Sealable, moisture-proof packaging is required for such wet wipes to keep the wipes from drying out through evaporation of the liquid medium and to aid in the transport of the wet wipe.

Other wipers provide the utility of additional substances in a dry wiper form. Often these substances are encapsulated and applied to the surface of the wiper or impregnated into the fibrous structure of the wiper, or they are encapsulated by pockets formed by, or in, the layers of a laminate wiper structure. For example, U.S. Pat. No. Re 32,713 to Woo (Original U.S. Pat. No. 4,514,461) teaches an encapsulated fragrance that is applied to the surface of the fabric or is impregnated within the interstices of the fibers of the fabric. Examples of a substance encapsulated by the layers of the laminate structure of the wiper can be found in U.S. Pat. No. 4,259,383 Eggensperger et al.; U.S. Pat. No. 4,515,703 to Haq; and U.S. Pat. No. 4,600,620 to Lloyd et al.; as well as in U.S. Patent Publication 2002/0039867 to Curro et al.

The functional substance that is contained in these wipers is released in a number of ways. First, for the wipes that are delivered in the wet form, the wipes are generally ready for use when removed from their packages. In some instances the stresses of dispensing can release encapsulated materials that have been additionally included, as U.S. Pat. No. 4,904,524 indicates. However, such wet wipes often require cumbersome packaging and if such packaging is not sealed properly may result in dried-up and useless wipes.

Wipes that are delivered in a dry state generally release the active ingredient by either the addition of a liquid or by the addition of pressure. U.S. Pat. No. 4,259,383 is an example of a disinfecting tissue where the active ingredient is activated when it is contacted with water. In U.S. Pat. Nos. 4,600,620 and 4,515,703 and U.S. Patent Publication 2002/0039867 all have an active agent encapsulated within the layers of their respective laminate structures. In these cases, the active agent is released when pressure is applied to the laminate structure. The agent is released through weakened bonds in the substrate or through perforations.

SUMMARY OF THE INVENTION

In light of the problems and issues discussed above, there is a desire for a wipe that is easily transportable in a dry state, having one or more functional agents whose release can be triggered by one or more types of triggering events.

The present invention is directed to a substantially dry wiper made of a first and second substantially dry substrate webs joined together in a face-to-face configuration. The wiper has at least one primary capsule disposed between the substrate webs and that encapsulates a primary agent. The primary agent is released from the primary capsule to the substrate webs upon the occurrence of a primary triggering event.

In various embodiments the first substrate web may be a nonwoven web. The wiper may contain cellulose fibers. In some embodiments the first and second substrate webs may be made of the same materials or may be made of different materials.

In some embodiments the wiper may have a plurality of primary microcapsules disposed between the first substrate web and the second substrate web that forms a layer of primary microcapsules over a distinct area of the wiper, and where the primary microcapsules contain the primary agent.

In some embodiments the primary agent may be selected from the group containing: water, cleaning solution, soap, degreaser, disinfectant, sanitizer, antibacterial substance, moisturizer, emollient, medicine, pH buffer, indicator, cosmetic, beauty care substance, or the like.

In some embodiments, the primary triggering event may be selected from the group containing: applied pressure, atmospheric pressure, temperature, moisture, pH, or contact with a specific substance. In specific embodiments the primary triggering event may be contact with water, urea, alcohol, an organic solvent, an acid, a base, or other specific liquid. In one embodiment, the primary triggering event may be the rolling of the wiper and twisting the opposite ends of the rolled wiper in opposite rotations in relation to each other.

In various embodiments, the wiper may additionally have at least one secondary capsule where the primary capsule is disposed between the first and second substrate webs and contains a secondary agent. In these embodiments, the secondary agent is different that the primary agent, and secondary agent is released from the secondary capsule to the first and second substrate webs upon the occurrence of a secondary triggering event. In some embodiments the wiper may have a plurality of secondary microcapsules, containing a secondary agent, disposed between the first and second substrate webs forming a layer of secondary microcapsules over a distinct area of the wiper. In either of these embodiments the primary triggering event may be the same or may different than the secondary triggering event. In one embodiment, the secondary triggering event is contact with the primary agent.

The invention is also directed to a method of cleaning a surface with a substantially dry wiper. The method includes the steps of providing a substantially dry wiper, as discussed above, exposing the primary capsule of the wiper to a primary triggering event to release the primary agent to the first and second substrate webs, and cleaning the surface with the wiper.

DETAILED DESCRIPTION

The wiper of the present invention includes a first substrate web and a second substrate web that are joined together in a face-to-face configuration. The substrate webs of the wiper are intended to be substantially dry such that the wiper is substantially dry when delivered to the user. At least one capsule is disposed between the first and second substrate webs and contains an agent. The agent is fully encapsulated by the capsule and such capsules are fully self-sustaining. The capsules do not require the substrate webs to encapsulate the agent therein, nor do they need the webs to initiate the release of said agents.

However, the substrate webs join to form the wiper of the invention and sandwich the one or more capsules there between, providing a convenient delivery mechanism for the capsules and the agents they contain. The substrate webs also provide exterior surfaces upon which the released agent may spread and which can provide the user with an appropriate amount of wiper surface area to use in personal cleansing or in cleaning a surface.

By their fully-contained and self-sustaining nature, capsules having different kinds of encapsulated agents may easily be included in a single wiper. Additionally, the material used to encapsulate the different agents may be designed to release the agents based on different triggering events. For example, the wiper of the present invention may include water as an encapsulated agent, encapsulated by a pressure-activated encapsulant, and soap as a second agent, encapsulated by a water-activated encapsulant. Such a wiper could be activated by releasing the water by applying pressure to the water-containing capsules, the released water would then trigger the soap containing capsules, resulting in a soapy wiper with which the user may cleanse.

As used herein, the terms "encapsulate", "encapsulated", and "encapsulating" refer to the agent being enclosed within the capsule. Similarly, as used herein, the term "encapsulant" refers to the substance that acts to encapsulate the agent. Additionally, as used herein, the term "wipe(s)" and "wiper(s)" are used interchangeably and refer to articles, substrates and laminates of substrates that are used to wipe surfaces including, but not limited to, human hair or skin, hard surfaces, and the like.

Figure 1:
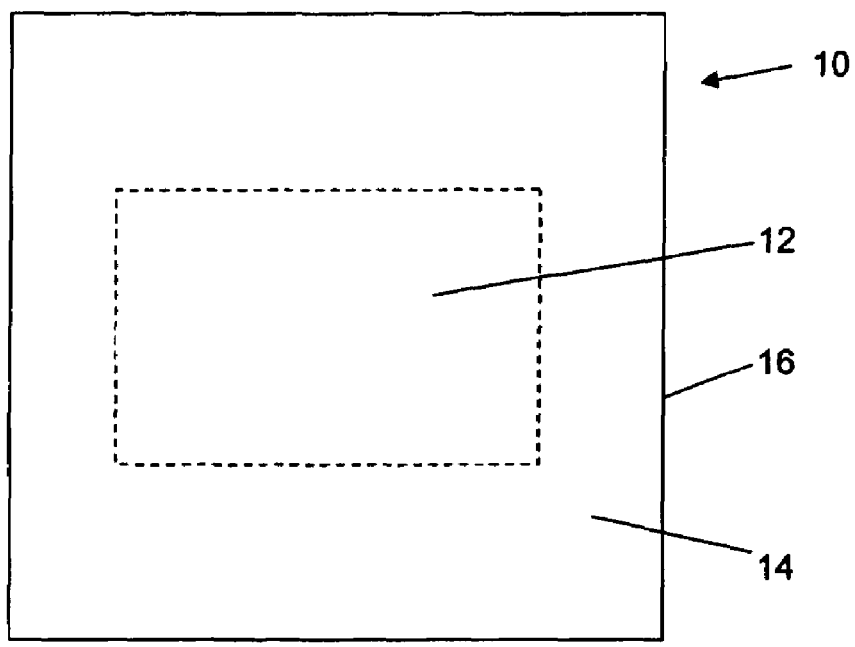
FIG. 1 is a plain view of an embodiment of the wiper of the present invention.

As shown in FIG. 1, the wiper 10 may be a generally rectangular shape defined by a periphery 16. The size and shape of the wiper 10 may be any size and shape that is desired as fits its designed purpose and is a matter of design preference. The shape of the wiper 10 may be symmetrical or asymmetrical.

The wiper 10 may be delivered to the user in a flat form as shown in FIG. 1. Alternatively, the wipers 10 may be delivered as a smaller, folded configuration, for the convenience of the user. For example, the wiper may be uniquely folded in such a way as to make a compactly-folded wiper easy for a user to grasp and open, such as described in U.S. patent application Ser. No. 10/021,404 by Reddy et al., filed Dec. 23, 2004. In either case, the wiper 10 may be individual, single wipers or may be in a stack of such wipers 10. The wiper 10 within the stack of wipers may additionally be interfolded to aid in dispensing.

Figure 4A:
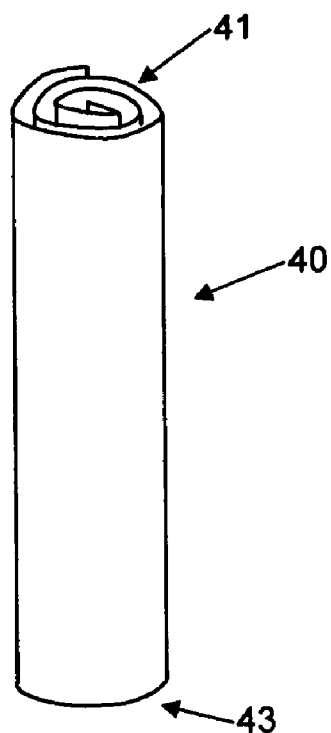
FIG. 4A is a perspective view of an embodiment of the wiper of the present invention as delivered in a rolled format.
Figure 4B:
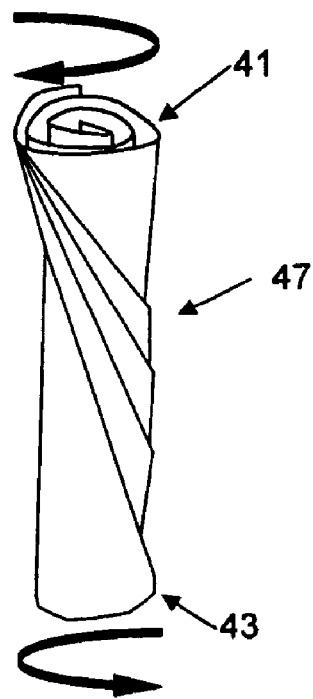
FIG. 4B is a perspective view of the embodiment of FIG. 4A being activated by twisting the ends of the rolled wiper.

Additional methods of delivering the wiper to users may address the method of triggering the release of the agent. For example, one embodiment of the present invention, as shown in FIGS. 4A and 4B, is to deliver the wiper in a rolled wiper 40 configuration. Such a rolled wiper 40 may be formed by rolling up a flat or folded wiper 10. In the rolled form, the wiper is a compact form which is easily stored and transported by the user. If such a rolled wiper 40 contains pressure-sensitive encapsulants, the encapsulated agent may be easily released by applying torsional forces to the rolled wiper 40 by twisting the first end 41 of the rolled wiper 40 in the opposite rotational direction than the second end 43 is twisted. The torsional force present in the twisted wiper 47 may then cause the agent to be released from pressure-sensitive capsules.

Other configurations and manners in which the wiper 10 may be delivered to the user may be possible, the examples of configurations given above are merely exemplary in nature and are not intended to be limiting. The desire is to deliver the user with a dry wiper without the need of specialized packaging, as is common with wet wipes. However, specialized packaging may be used to aid in dispensing or to add additional functionality to such a wiper.

Wipers may be useful for personal, household, commercial and industrial cleansing applications. Substrate webs 14 used to form a wiper of the type contemplated here are generally well known in the industry. Such substrate webs 14 may include natural fibers, such as cellulosic fibers, synthetic fibers and polymers, or combinations thereof. These fibers are converted into substrate webs 14 by a variety of processes that are also generally well known in the industry. Wipers can be made of substrate webs 14 that are a single layer web or may be made of substrate webs 14 made of multiple layers. A substrate web 14 made of multiple layers may have similar materials in each layer or may be made of differing layers.

It is intended that the substrate webs 14 of the present invention be substantially dry and the resulting wiper 10 be substantially dry when delivered to the user. As used herein, the term "substantially dry" refers to the web being free of liquid and all but ambient moisture.

The wiper 10 is made from two of such substrate webs 14 that are joined together in a face-to-face configuration. At least one encapsulated agent is sandwiched between the two substrate webs. The two substrate webs 14 used to make the wiper 10 may be the same type of material (i.e., materials made by the same type of process) or they may be different types of materials. The substrate webs 14 may be made of the same type of fibers (i.e., natural fibers, synthetic fibers, etc.) or they may be made of different types of fibers. The substrate webs 14 need to be compatible with the encapsulated agents to be released and the encapsulant used.

Additionally, the substrate webs 14 must have the appropriate level of porosity. The released agent must be capable of easily migrating from the centralized location of the encapsulated agents in the center of the wiper 10 to the surfaces of the wiper 10 for use by the user. The substrate webs 14 are not intended to act as an encapsulant to the agents; the substrate webs 14 act as a convenient transport medium for the capsules and further act as helpful carrier for the agent when released from the capsules. Any substrate web 14 that could act as a encapsulant (e.g., non-porous and non-apertured polymeric films) would act against the purposes of the present invention if used as both substrate webs 14; the agent would prevented from traveling from its central location within the wiper 10 to the surface of the wiper 10.

The substrate webs 14 may be nonwoven webs, woven webs or knitted webs, as are well-known in the art. The substrate web materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins and many other materials. The fibers may be relatively short, staple length fibers, typically less than 3 inches, or longer and substantially more continuous fibers such as are produced by spunbonding and meltblowing processes.

An example of a material that may used for the substrate webs 14 of the wiper 10 of the invention are the hydroentangled materials commonly used in such wipers and sold by the Kimberly-Clark Corporation, Roswell, Ga., as HYDROKNIT®. Examples of such hydroentangled materials are discussed in U.S. Pat. No. 5,284,703 to Everhart et al., U.S. Pat. No. 5,389,202 to Everhart et al., U.S. Pat. No. 6,103,061 to Anderson et al., and U.S. Pat. No. 6,784,126 to Everhart et al.

The substrate webs 14 may be coform materials such as shown in U.S. Pat. No. 4,818,464 to Lau and U.S. Pat. No. 4,100,324 to Anderson et al. The substrate webs 14 may be spunbond materials as are well known in the art and as shown in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, and U.S. Pat. No. 3,542,615 to Dobo et al.

Other non-limiting examples of materials that can be used as web substrates 14 in the wiper 10 of the present invention are disclosed in U.S. Pat. No. 4,820,577 to Morman et al., U.S. Pat. No. 4,950,526 to Singleton, U.S. Pat. No. 5,350,624 to Georger et al., U.S. Pat. No. 6,331,230 to Hermans et al., U.S. Pat. No. 6,149,767 to Hermans et al., U.S. Pat. No. 6,177,370 to Skoog et al., U.S. Pat. No. 6,649,547 to Arnold et al., U.S. Pat. No. 6,692,825 to Qin et al., U.S. Pat. No. 6,736,916 to Steinke et al., U.S. Pat. No. 6,777,056 to Boggs et al., U.S. Pat. No., U.S. Pat. No. 6,797,360 to Varona, and U.S. Pat. No. 6,797,377 to DeLucia et al.

The wiper 10 of the present invention contains one or more capsules which encapsulate an agent or agents for use with the wiper 10. The capsules may be any size that is appropriate for the particular wiper 10 and the agent contained within the capsule or capsules. Such capsules may range in magnitude from similar to the size of the wiper 10, to smaller macro-capsules, and to even smaller micro-capsules. As shown in FIG. 1, the wiper 10 may incorporate a single large capsule 12 between the substrate webs 14 of the wiper 10. Such large capsules are on the same order of magnitude in size as the wiper 10. Large capsules 12 may have the same area as the wiper 10 or may be some smaller percentage of the area of the wiper 10. For example, the large capsule 12 may be 60 percent of the area of the wiper 10, 50 percent of the area of the wiper 10, 30 percent of the area of the wiper 10, 25 percent of the area of the wiper 10, or may even be a smaller percentage of the area of the wiper 10. Such large capsules 12 are of a size that they can easily be found, either visually or tactilely, when the user handles the wiper 10.

The large capsule 12 may be centrally located as shown in FIG. 1 or may be located off-center, at an edge, in a corner, or some other location. The location of the large capsule 12 is primarily a design preference and may be located wherever appropriate for the purpose and manner of use for such a wiper 10.

Figure 2:
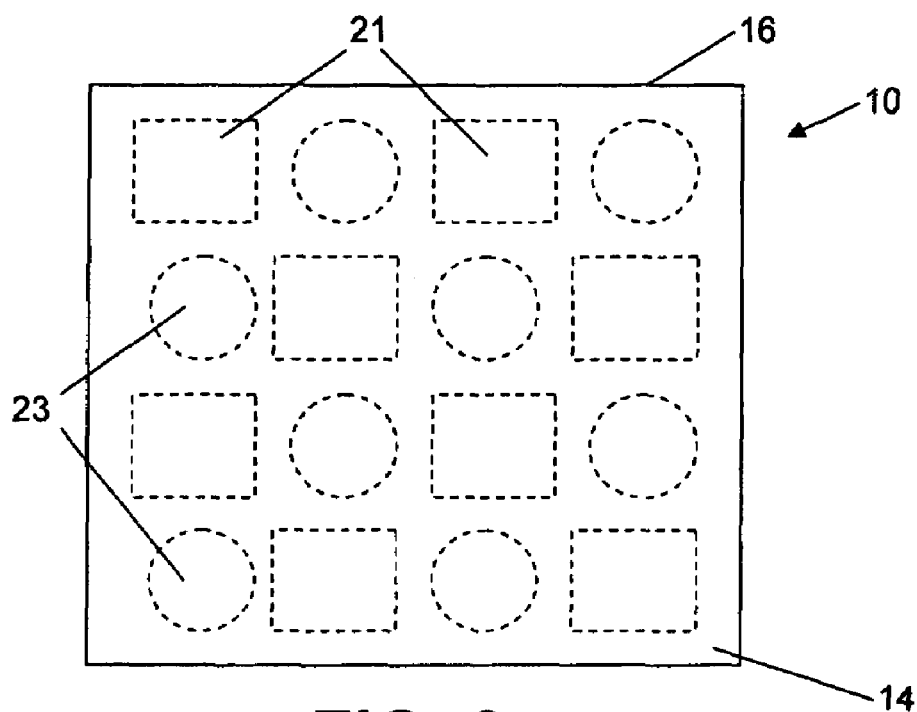
FIG. 2 is a plain view of another embodiment of the wiper of the present invention.

In another embodiment of the invention, as shown in FIG. 2, the wiper 10 may have multiple macro-capsules 21, 23 present between the web substrates 14. Such macro-capsules would be on the same order of magnitude as the area of the wiper 10 itself, but smaller than the area of the wiper 10. The macro-capsules 21, 23 would be of a size that can easily be found, either visually or tactilely, when the user handles the wiper 10. Each of such marco-capsules 21, 23 are distinct and separate from each other. The multiple macro-capsules 21, 23 may be the same shape and size as each other or they may be different shapes and sizes.

FIG. 2 illustrates a wiper 10 having multiple marco-capsules. As shown, there are multiple primary macro-capsules 21 and multiple secondary macro-capsules 23. Both the primary and secondary macro-capsules 21, 23 may use the same type or different types of encapsulants and may contain the same or different agents.

The primary and secondary macro-capsules 21, 23 are shown as occupying the majority of the area of the wiper 10 in an alternating pattern of primary macro-capsules 21 and secondary macro-capsules 23. The macro-capsules 21, 23 may instead only occupy a portion of the area of the wiper 10, such as a single half of the wiper 10, or a corner section of the wiper 10. Rather than an alternating pattern of macro-capsules, the primary macro-capsules 21 may be segregated to a different area of the wiper 10 than the secondary macro-capsules 23.

Additionally, more than just two types of macro-capsules 21, 23 may be present in the same wiper 10. For example, a square wiper 10 may divided into four quadrants such that a different type of macro-capsule (e.g., a different encapsulated agent) is segregated into each of the four quadrants. Greater numbers of macro-capsules may be present in the wiper. The number of types of macro-capsules, their size and shape, the encapsulated agent within the micro-capsule, and their placement within wiper 10 are a matter of design preference and may be located wherever appropriate for the purpose and manner of use of such a wiper 10.

Figure 3:
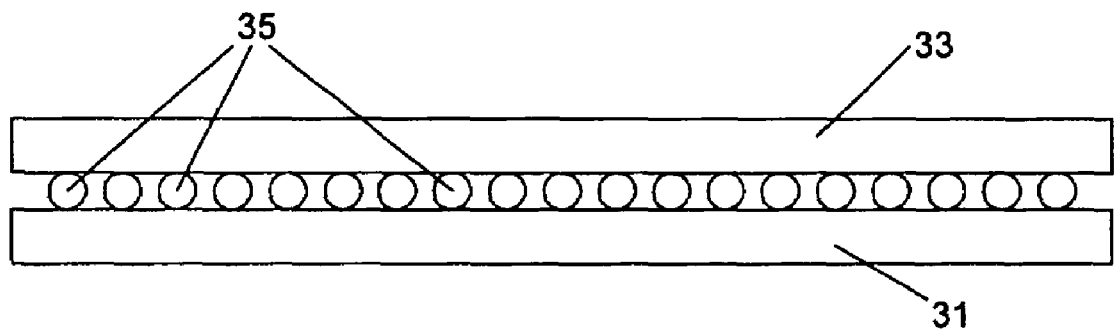
FIG. 3 is a side cross-sectional view of another embodiment of the wiper of the presenting invention.

Another embodiment of the invention is a wiper 10 may have even smaller capsules sandwiched between the substrate webs 14 of the wiper. The agent or agents of the wiper 10 may be encapsulated in a plurality of micro-capsules 35, as shown in FIG. 3. Such micro-capsules are orders of magnitude smaller than the wiper itself and may be difficult to see, or tactilely find, when the user handles the wiper 10. Such micro-capsules 35 are typically substantially spherical in shape and in the size range of 100 nm and 3 mm in diameter.

The plurality of micro-capsules 35 may form a layer of micro-capsules 35, between the first substrate web 31 and the second substrate web 33, which encompasses the entire area of the wiper 10. Alternatively, the micro-capsules 35 may be present in a small single area of the wiper 10 or may be present in multiple discontinuous areas throughout the area of the wiper 10.

The micro-capsules 35 may all contain the same agent or they may contain two or more different agents. In some embodiments, micro-capsules 35 may encapsulate different types of agents and such micro-capsules 35 may be randomly mixed through out the plurality of such micro-capsules 35. In other embodiments, micro-capsules 35 having the same agent may be segregated to different areas of the wiper 10 than other micro-capsules 35 having a different agent.

The wipers 10 of the present invention will generally be assembled by first applying the capsule or capsules to a first substrate web. A second substrate web is then applied on top of first substrate web and capsule(s). The substrate webs are bonded together to form the finished wiper 10 with the capsules, containing the agent(s), located between the substrate webs.

The substrate webs may be joined together to form the finished wiper 10 by those methods that are generally known in the art to bond such substrate webs. Generally, the substrate webs will be joined by adhesive bonding, thermal bonding, ultrasonic bonding, or combinations of such bonding methods.

Adhesive bonding is the preferred method of bonding for capsules that are sensitive to pressure and/or temperature. Additionally, some degree of adhesive bonding may be used to adhere the capsules to the first substrate web when constructing the wiper 10 in conjunction with thermal, ultrasonic or adhesive bonding to join the substrate webs. The adhesive amount used may vary from a thin film coating a few microns thick to a thickness equivalent to the size of the capsule (i.e., completely immobilizing the capsule). The actual amount and type of adhesive used will depend on the size of the wiper 10, the relative materials of the substrate webs 14 and capsules and the encapsulated composition. The adhesive must be compatible with the substrate webs 14, encapsulant and encapsulated formulation, and the ready release of the encapsulated formulation upon release from the capsule.

Examples of adhesives that may used to bond the substrate webs 14 together and/or bond capsules to the substrate webs 14 include, but is not limited to, adhesives made of urethane, acrylic or epoxy, fluorine-based adhesives, silicone-based adhesives, hot melt adhesives, and other adhesives as are well known in the art. Such adhesives are readily available from companies such as 3M, St. Paul, Minn.; Dow Chemical Corporation, Midland, Mich.; National Starch & Chemical, Bridgewater, N.J.; and other similar companies.

For substrate webs 14 that contain some degree of thermoplastic fibers, thermal or ultrasonic bonding may be used.

When the wiper 10 has micro-capsules 35, the micro-capsules 35 and the substrate web 14 may cooperate in forming the wiper 10. When appropriately sized, the micro-capsules 35 may be held in the interstices between the individual fibers that make up the surface of the substrate web 14 on which the micro-capsules 35 are placed. As such, no additional bonding may be required to hold the micro-capsules 35 in place. However, some small amount of adhesive may be applied with the micro-capsules 35 to ensure that they are secured to the substrate web 14.

In another embodiment, one or both of the substrate webs 14 may be textured; having a plurality of alternating peaks and valleys. In such embodiments, the micro-capsules 35 may be placed on the first substrate web 31 in such a way as the vast majority of micro-capsules 35 are located in the valleys of the first substrate web 31 surface. The second substrate web 33 may then be bonded to the first substrate web 31 at those points where the second substrate web 33 contacts the peaks of the surface of the first substrate web 31.

Capsules may be formed by any of the processes that are well known in the art to encapsulate the agent compositions discussed above. For example larger capsules or macro-capsules may be formed as pouches of thermoplastic materials that are thermally sealed at the edges. Nonlimiting examples of methods of producing the micro-capsules include mechanical punching as described in U.S. Pat. No. 6,238,616 to Ishikawa et al., coacervation process as are described in U.S. Pat. No. 4,777,089 to Takizawa et al., U.S. Pat. No. 3,943,063 to Morishita et al. and U.S. Pat. No. 4,978,483 to Redding, Jr.; and by extrusion as discussed in U.S. Pat. No. 3,310,612 to Somerville, Jr.; U.S. Pat. No. 3,389,194 to Somerville; U.S. Pat. No. 2,799,897 to Jansen; U.S. Pat. No. 5,385,737 to Shigeno et al.; and U.S. Pat. No. 5,330,835 to Kikuchi et al. More particularly, the capsules may be manufactured by the methods as disclosed in U.S. patent application Ser. No. 10/954,312 to Reddy et al., filed Sep. 30, 2004.

It is desired that the encapsulant that encapsulates the agent compositions discussed above would contain the agent and release that same agent upon occurrence of a trigger specific to that encapsulant. As used herein, the term "trigger" refers to an event which initiates the release of the encapsulated agent from the capsule. Of particular interest for the encapsulated agents of the wipers of the present invention are capsules that may be triggered by changes in pressure, moisture or water, temperature, pH, environmental factors, and the like.

The various agent compositions may be combined with any compatible encapsulant trigger. For example, an encapsulant with a water-soluble trigger would not be suitable with a water-based agent composition without additional water-insoluble coating made to the interior of the capsule that can cooperate with the exterior water-soluble triggered encapsulant. Such a water-insoluble coating would then prevent the water-based agent contained within the capsule from triggering the capsule from within. As intended, the capsule would only be triggered by water outside of the capsule.

One type of possible encapsulant for use with the present invention are those materials having a pressure related trigger. Such materials will initiate release of the encapsulated agent composition upon experiencing a change in pressure experienced by the encapsulant (i.e., application of pressure or change in atmospheric pressure). Such encapsulants may be ruptured via pressure, which results in a structural failure and releases the active encapsulated within the capsule.

Examples of shell encapsulant materials having a pressure related trigger include aqueous based materials like, poly vinyl alcohols, gelatin and its derivatives, cellulose and its derivatives, starches and their various derivatives, arabic gum, salts of algin, salts of chitin, carrageenan, chitosan and its derivatives.

Other pressure triggered encapsulants may include discontinuous systems such as network structures of poly(methyl methacrylate), poly(butyl methacrylate), poly(hydroxyethyl methacrylate) di and tri block copolymers. Additional such discontinuous systems include hydrogels of poly ethylene glycol (PEG).

Another class of pressure triggered encapsulants are molten systems. Such molten systems may include waxes (paraffin, crystalline, microcrystalline or a combination thereof) in the molecular weight range of 50,000 to 60,000 daltons. Additional examples of useful molten systems would include low density polyethylene (LDPE), high density polyethylene (HDPE), polypropylene, and other types of pressure sensitive plastics such as rubber, latex, and the like.

Any of the above materials either separate or in combination (chemically, physical blend or laminated layers) with each other could act as a material for the capsules.

Another type of possible encapsulant for use with the present invention are those materials having a moisture or water related trigger. Such materials will initiate release of the encapsulated agent composition upon exposure to some level of moisture or exposure to liquid.

Such encapsulating material may be made of synthetic water soluble polymers like polyurethane, polyvinyl alcohols (manufactured by SNP Inc, with offices in Durham, N.C.) in combination with cellulose or cellulose derivatives for added strength and functionality. Some of the above mentioned pressure sensitive materials are also water sensitive like gelatin, cellulose and starch based materials.

Other moisture sensitive materials include poly(hydroxyl alkanates) (PHA's), poly lactic acid, poly glycolic acid, poly lactic-co-glycolic acid, and their corresponding derivatives.

Examples of water soluble or water dispersible polymers that can be used as encapsulants are described in U.S. Pat. No. 4,777,089 to Takizawa et al.; U.S. Pat. No. 4,898,781 to Onouchi et al.; U.S. Pat. No. 4,908,233 to Takizawa et al.; and U.S. Pat. No. 5,064,650 to Lew.

Examples of encapsulant material that can be triggered by temperature include waxes (paraffin, crystalline, microcrystalline or a combination thereof) having a molecular weight in the range of 600 to 200,000 daltons. Other temperature-triggered encapsulants may include copolymers based on N-isopropylacrylamide (NIPAAm) and glucosyoxylethyl methacrylate (GEMA) and copolymers based on N-isopropylacrylamide (NIPAAm) and other functional moieties The sensitivity to hot or cold temperatures of such temperature-triggered encapsulant may be altered by changing the molecular weight and or blend/copolymer concentration.

Another type of possible encapsulant for use with the present invention are those materials having a pH related trigger. Such materials would initiate release of the encapsulated agent composition upon exposure to some level or change in pH. For example, this may be particularly useful in hospital settings where hands are cleansed using an alcohol-based cleanser which can dry the skin. A capsule that uses a pH sensitive encapsulant could then be triggered and release an emollient composition.

Example of encapsulants that may be used with a pH trigger may include copolymers based on N-isopropylacrylamide (NIPAAm) and other functional moieties, blends and or copolymers of poly(propylacrylic acid) (PPAA), and copolymers of 4-amino-N-[4,6-dimethyl-2-pyrimidinyl]benzene sulfonamide and N,N-dimethylacrylamide.

It is contemplated that other environmental changes could be used as triggers for the encapsulants. For example light sensitive polymers such as poly(ketones), polyacrylates, polymethacrylates and their blends and/or copolymers or copolymers may be used to release agents upon exposure to light.

The wiper 10 of the present invention include one or more agents that are encapsulated and held between the substrate webs 14 of the wiper 10 until they are released into the substrate webs 14. Various agents may provide various functionalities to the wipers 10 of the invention. Such agents may include water, cleaning solution, soap, degreaser, disinfectant, sanitizer, antibacterial substance, moisturizer, emollient, medicine, pH buffer, indicator, cosmetic, beauty care substance, or the like. Specific examples of cleansers, therapeutic benefit agents, or surface cleaners are discussed below and are intended to be exemplary, rather than limiting, in nature.

Cleansers

Surfactants, particularly those characterized as lathering surfactants may be encapsulated for use as a cleansing agent in the present invention to provide easy and rapid foam generation at surfactants levels desirable to provide skin mildness of the cleansing wiper. Generally the wipers containing such encapsulated lathering surfactants will contain encapsulated surfactants at a level from about 0.01% to 500%, by weight of the substrate webs prior to the addition of the encapsulated surfactant. Alternatively, the wipers of the present invention comprise surfactants at levels from about 0.05% to about 75%, alternatively from about 0.06% to about 50%, and finally from about 0.07% to about 25%, based on the weight of the substrate webs prior to the addition of the encapsulated surfactant.

By a "lathering surfactant" is meant a surfactant, that when combined with water and mechanically agitated generates a foam or lather. As such, it is intended that such a wiper 10 containing encapsulated lathering surfactants would be used with a water source or, as discussed above, water could be included in the same wiper 10 as another agent. These surfactants should be mild, which means that they provide sufficient cleansing or detersive benefits but do not overly dry the skin or hair (e.g., removing too much natural oil and/or moisture).

A wide variety of lathering surfactants are useful herein and include those selected from the group consisting of anionic lathering surfactants, nonionic lather surfactants, amphoteric lathering surfactants, and mixtures thereof. Generally, the lathering surfactants do not strongly interfere with deposition of any skin care active and, or conditioning agents that are present, e.g., are fairly water soluble, and usually have an HLB value of above 10. Cationic surfactants can also be used as optional components, provided they do not negatively impact the overall lathering characteristics of the required lathering surfactants. Additionally, co-surfactants may be present in the lathering surfactant composition, as stabilizers.

Anionic Lathering Surfactants

A wide variety of anionic lathering surfactants are useful as encapsulated agents of the wipers of the present invention. Nonlimiting examples of anionic lathering surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulas ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

wherein R$_1$ is chosen from the group consisting of a straight or branched chain, saturated aliphatic hydrocarbon radical having from about 8 to about 24, alternatively about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts) of fatty acids, typically having from about 8 to about 24 carbon atoms, alternatively from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853 to Collins.

Other anionic materials include phosphates such as monoalkyl, dialkyl, and trialkylphosphate salts.

Other anionic materials include alkanoyl sarcosinates corresponding to the formula RCON(CH$_3$)CH$_2$CH$_2$CO$_2$M wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates that are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072 to Kosmin. Further nonlimiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between $C_8$ and $C_{16}$. Nonlimiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are glutamates, especially those having carbon chains between $C_8$ and $C_{16}$. Nonlimiting examples of glutamates include ammonium, sodium, potassium and alkanolamine (e.g., triethanolamine) salts of lauroyl glutamate, myristoyl glutamate, and cocoyl glutamate.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein are ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Other known anionic lathering surfactants useful in the encapsulated compositions of the wipers of the present invention may be found in McCutcheon's, Detergents and Emulsifiers, North American edition (1986), published by Allured Publishing Corporation; McCutcheon's, Functional Materials, North American Edition (1992); and U.S. Pat. No. 3,929,678, to Laughlin et al.

Nonionic Lathering Surfactants

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Alkyl glucosides and alkyl polyglucosides are useful herein, and can be broadly defined as condensation articles of long chain alcohols, e.g. $C_{8-30}$ alcohols, with sugars or starches or sugar or starch polymers, i.e., glycosides or polyglycosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

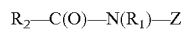

wherein: $R_1$ is H, $C_1$-$C_4$ alkyl, 2-hydroxyethyl, 2-hydroxypropyl, alternatively $C_1$-$C_4$ alkyl, more alternatively methyl or ethyl, most alternatively methyl; $R_2$ is $C_5$-$C_{31}$ alkyl or alkenyl, alternatively $C_7$-$C_{19}$ alkyl or alkenyl, more alternatively $C_9$-$C_{17}$ alkyl or alkenyl, most alternatively $C_{11}$-$C_{15}$ alkyl or alkenyl; and Z is a polhydroxyhydrocarbyl moiety having a linear hydrocarbyl chain with a least 3 hydroxyls directly connected to the chain, or an alkoxylated derivative (alternatively ethoxylated or propoxylated) thereof. Z alternatively is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R_2CO$— moiety is derived from coconut oil fatty acids). Processes for making compositions containing polyhydroxy fatty acid amides are disclosed, for example, in U.S. Pat. No. 2,965,576 to Wilson; U.S. Pat. No. 2,703,798 to Schwartz; and U.S. Pat. No. 1,985,424 to Piggott.

Other examples of nonionic surfactants include amine oxides. Amine oxides correspond to the general formula $R_1R_2R_3N{\rightarrow}O$, wherein $R_1$, contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in the capsules of this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Nonlimiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide, and mixtures thereof.

Other known examples of nonionic lathering surfactants for use in the encapsulated compositions of the wipers of present invention are discussed in McCutcheon's, Detergents and Emulsifiers, North American edition (1986), published by allured Publishing Corporation; and McCutcheon's, Functional Materials, North American Edition (1992).

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the encapsulated compositions of the wipers of the present invention. Particularly useful are those which are broadly described as derivatives of aliphatic secondary and tertiary amines, alternatively wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, cetyl dimethyl betaine (available as Lonzaine 16SP from Lonza, Inc. of Allendale, N.J.), lauryl bis-(2-hydroxyethyl) carboxymethyl betaine, oleyl di-methyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc of Cranbury, N.J.).

Preferred for use herein are amphoteric surfactants having the following structure:

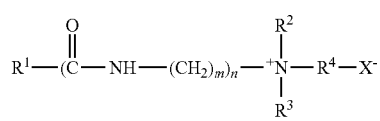

wherein $R_1$ is unsubstituted, saturated or unsaturated, straight or branched chain alkyl having from about 9 to about 22 carbon atoms. Preferred $R_1$ has from about 11 to about 18 carbon atoms; more alternatively from about 12 to about 18 carbon atoms; more alternatively still from about 14 to about 18 carbon atoms; m is an integer from 1 to about 3, more alternatively from about 2 to about 3, and more alternatively about 3; n is either 0 or 1, alternatively 1; $R_2$ and $R_3$ are independently selected from the group consisting of alkyl having from 1 to about 3 carbon atoms, unsubstituted or mono-substituted with hydroxy, preferred $R_2$ and $R_3$ are $CH_3$; X is selected from the group consisting of $CO_2$, $SO_3$ and $SO_4$; $R_4$ is selected from the group consisting of saturated or unsaturated, straight or branched chain alkyl, unsubstituted or monosubstituted with hydroxy, having from 1 to about 5 carbon atoms. When X is $CO_2$, $R_4$ alternatively has 1 or 3 carbon atoms, more alternatively 1 carbon atom. When X is $SO_3$ or $SO_4$, $R_4$ alternatively has from about 2 to about 4 carbon atoms, more alternatively 3 carbon atoms.

Examples of amphoteric surfactants of the encapsulated composition of the wipers of the present invention include the following compounds: cetyl dimethyl betaine (this material also has the CTFA designation cetyl betaine), wherein R has from about 9 to about 13 carbon atoms; and cocamidopropyl hydroxy sultaine, wherein R has from about 9 to about 13 carbon atoms, Examples of other useful amphoteric surfactants are alkyliminoacetates, and iminodialkanoates and aminoalkanoates of the formulas $RN[(CH_2)_mCO_2M]_2$ and $RNH(CH_2)_mCO_2M$ wherein m is from 1 to 4, R is a $C_8$-$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 to Lynch; and the products sold under the trade name "Miranol" and described in U.S. Pat. No. 2,528,378 to Mannheimer. Other examples of useful amphoterics include amphoteric phosphates, such as coamidopropyl PG-dimonium chloride phosphate (commercially available as Monaquat PTC, from Mona Industries of Paterson, N.J.). Also useful are amphoacetates such as disodium lauroamphodiacetate, sodium lauroamphoacetate, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

Other known examples of amphoteric surfactants useful in the encapsulated compositions of the wipers of the present invention are disclosed in McCutcheon's, Detergents and Emulsifiers, North American edition (1986), published by allured Publishing Corporation; and McCutcheon's, Functional Materials, North American Edition (1992).

Co-Surfactants

The encapsulated cleansing compositions of the wipers of the present invention may optionally contain one or more co-surfactants as stabilizers for the encapsulated cleansing compositions. Ideally, the co-surfactants will contribute to the cleansing and lathering capabilities of the resultant composition, but is not a requirement of their stabilizing function. Preferably, these co-surfactants will also be lathering surfactants and may be selected from the group consisting of anionic lathering surfactants, nonionic lathering surfactants, cationic lathering surfactants, amphoteric lathering surfactants, and combinations thereof.

Nonlimiting examples of anionic lathering surfactants useful as stabilizing co-surfactants in the encapsulated compositions of the wiper of the present invention are disclosed in U.S. Pat. No. 3,929,678 to Laughlin et al. A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and combinations thereof.

Nonlimiting examples of nonionic lathering surfactants for use as stabilizing co-surfactants in the encapsulated compositions of the wipers of the present invention include those selected from the group consisting of alkyl glucosides, alkyl polyglucosides, polyhydroxy fatty acid amides, alkoxylated fatty acid esters, sucrose esters, amine oxides, and mixtures thereof.

Nonlimiting examples of cationic lathering surfactants for use as stabilizing co-surfactants in the encapsulated compositions of the wipers of the present invention include, but are not limited to, fatty amines, di-fatty quaternary amines, tri-fatty quaternary amines, imidazolinium quaternary amines, and combinations thereof. Suitable fatty amines include monalkyl quaternary amines such as cetyltrimethylammonium bromide. A suitable quaternary amine is dialklamidoethyl hydroxyethylmonium methosulfate. The fatty amines, however, are preferred. It is preferred that a lather booster is used when the cationic lathering surfactant is the primary lathering surfactant of the cleansing component. Additionally, nonionic surfactants have been found to be particularly useful in combination with such cationic lathering surfactants.

Nonlimiting examples of amphoteric or zwitterionic surfactants for use as stabilizing co-surfactants in the encapsulated compositions of the wipers of the present invention are those selected from the group consisting of betaines, sultaines, hydroxysultaines, alkyliminoacetates, iminodialkanoates, aminoalkanoates, and mixtures thereof.

Therapeutic Benefit Agent

The encapsulated compositions may optionally contain a safe and effective amount of therapeutic benefit agent such as vitamin compounds, skin treating agents, anti-acne actives, anti-wrinkle actives, anti-skin atrophy actives, anti-inflammatory actives, topical anesthetics, artificial tanning actives and accelerators, anti-microbial actives, anti-fungal actives, sunscreen actives, anti-oxidants, skin exfoliating agents, and combinations thereof. As used herein, "a safe and effective amount" means an amount of a compound or component sufficient to significantly induce a positive effect or benefit, but low enough to avoid serious side effects, (e.g., undue toxicity or allergic reaction), i.e., to provide a reasonable benefit to risk ratio, within the scope of sound medical judgment.

The optional components useful herein can be categorized by their therapeutic or aesthetic benefit or their postulated mode of action. It is to be understood, however, that the optional components useful herein can in some instances provide more than one therapeutic or aesthetic benefit or operate via more than one mode of action. Therefore, classifications herein are made for the sake of convenience and are not intended to limit the component to that particular application or applications listed. Also, when applicable, the pharmaceutically-acceptable salts of the components are useful herein.

Vitamin Compounds

The encapsulated composition may comprise vitamin compounds, precursors, and derivatives thereof. These vitamin compounds may be in either natural or synthetic form. Suitable vitamin compounds include, but are not limited to, Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds.

In particular, the encapsulated composition of the wipers of the present invention may comprise a safe and effective amount of a vitamin B3 compound. Vitamin B3 compounds are particularly useful for regulating skin condition as described in U.S. Pat. No. 6,238,678 to Oblong. The encapsulated compositions of the wipers of the present invention preferably comprise from about 0.01% to about 50% by weight of the composition, more preferably from about 0.1% to about 10%, even more preferably from about 0.5% to about 10%, and still more preferably from about 1% to about 5%, most preferably from about 2% to about 5%, of the vitamin B3 compound.

As used herein, "vitamin B3 compound" means a compound having the formula:

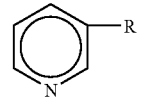

wherein R is —CONH$_2$ (i.e., niacinamide), —COOH (i.e., nicotinic acid) or —CH$_2$OH (i.e., nicotinyl alcohol); derivatives thereof; and salts of any of the foregoing.

Skin Treating Agents

The encapsulated composition of the wipers of the present invention may contain one or more skin treating agents. Suitable skin treating agents include those effective for preventing, retarding, arresting, and/or reversing skin wrinkles. Examples of suitable skin treating agents include, but are not limited to, alpha-hydroxy acids such as lactic acid and glycolic acid and beta-hydroxy acids such as salicylic acid.

Anti-Acne Actives

Examples of useful anti-acne actives for the encapsulated composition of the wipers of the present invention include, but are not limited to, the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives

Examples of anti-wrinkle and anti-skin atrophy actives useful for the encapsulated composition of the wipers of the present invention include, but are not limited to, retinoic acid and its derivatives (e.g., cis and trans); retinol; retinyl esters; niacinamide, salicylic acid and derivatives thereof; sulfur containing D and L amino acids and their derivatives and salts, particularly the N-acetyl derivatives, a preferred example of which is N-acetyl-L-cysteine; thiols, e.g., ethane thiol; hydroxy acids, phytic acid, lipoic acid; lysophosphatidic acid, and skin peel agents (e. g., phenol and the like).

Non-Steroidal Anti-Inflammatory Actives (NSAIDS)

Examples of NSAIDS useful for the encapsulated composition of the wipers of the present invention include, but are not limited to, the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics

Examples of topical anesthetic drugs useful for the encapsulated composition of the wipers of the present invention include, but are not limited to, benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Actives and Accelerators

Examples of artificial tanning actives and accelerators useful for the encapsulated composition of the wipers of the present invention include, but are not limited to, dihydroxyacetaone, tyrosine, tyrosine esters such as ethyl tyrosinate, and phospho-DOPA.

Antimicrobial and Antifungal Actives

Examples of antimicrobial and antifungal actives useful for the encapsulated composition of the wipers of the present invention include, but are not limited to, β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorocarbanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole.

Anti-Viral Agents

The encapsulated composition of the wipers of the present invention may further comprise one or more anti-viral agents. Suitable anti-viral agents include, but are not limited to, metal salts (e.g., silver nitrate, copper sulfate, iron chloride, etc.) and organic acids (e.g., malic acid, salicylic acid, succinic acid, benzoic acid, etc.). In particular compositions which contain additional suitable anti-viral agents include those described in U.S. Pat. No. 6,294,186 to Beerse et al.

Enzymes

The encapsulated composition of the wipers of the present invention may optionally include one or more enzymes. Preferably, such enzymes are dermatologically acceptable. Suitable enzymes include, but are not limited to, keratinase, protease, amylase, subtilisin, etc.

Sunscreen Actives

The encapsulated composition may also include sunscreening actives. Nonlimiting examples of sunscreens which are useful in the encapsulated compositions of the wipers of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyidibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Especially preferred examples of these sunscreens include those selected from the group consisting of 4-N,N-(2-ethylhexyl) methylaminobenzoic acid ester of 2,4-dihydroxybenzophenone, 4-N,N-(2-ethylhexyl)methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy)dibenzoylmethane, and mixtures thereof. Exact amounts of sunscreens which can be employed will vary depending upon the sunscreen chosen and the desired Sun Protection Factor (SPF) to be achieved.

A wide variety of known sunscreening agents are also described in U.S. Pat. No. 5,087,445 to Haffey et al.; U.S. Pat. No. 5,073,372 to Turner et al.; and U.S. Pat. No. 5,073,371 to Turner et al. Still other useful sunscreens are those disclosed in U.S. Pat. No. 4,937,370 to Sabatelli and U.S. Pat. No. 4,999,186, to Sabatelli et al.

Hydrocolloids

Hydrocolloids may also be optionally included in the encapsulated composition of the wipers of the present invention. Hydrocolloids are well known in the art and are helpful in extending the useful life of the surfactants contained in the encapsulated cleansing component of the wipers of the present invention such that the articles may last throughout at least one entire showering or bathing experience. Suitable hydrocolloids include, but are not limited to, xanthan gum, carboxymethyl cellulose, hydroxyethyl cellulose, hydroxylpropyl cellulose, methyl and ethyl cellulose, natural gums, gudras guar gum, bean gum, natural starches, deionitized starches (e.g., starch octenyl succinate) and the like.

Exothermic Zeolites

Zeolites and other compounds which react exothermically when combined with water may also be optionally included in the encapsulated composition of the wipers of the present invention.

Hydrogel Forming Polymeric Gelling Agents

In certain embodiments of the present invention, the encapsulated compositions may optionally comprise an aqueous gel, i.e., a "hydrogel", formed from a hydrogel forming polymeric gelling agent and water. More specifically, the hydrogel is contained within the cleansing component or the therapeutic benefit component of the article. When an aqueous gel is present, the articles preferably comprise from about 0.1% to about 100%, by weight of the substrate webs, more preferably from about 3% to about 50%, and most preferably from about 5% to about 35%, of a hydrogel forming polymeric gelling agent, calculated based on the dry weight of the hydrogel forming polymeric gelling agent.

Suitable hydrogel forming polymeric gelling agents in the form of particles are commercially available from Hoechst Celanese Corporation, Portsmouth, Va., USA (Sanwet® Superabsorbent Polymers) Nippon Shokubai, Japan (Aqualice®, e.g., L-75, L-76) and Dow Chemical Company, Midland, Mich., USA (Dry Tech®). Hydrogel forming polymeric gelling agents in the form of fibers are commercially available from Camelot Technologies Inc., Leominster, Mass., USA (Fibersorb®, e.g., SA 7200H, SA 7200M, SA 7000L, SA 7000, and SA 7300).

Chelators

The encapsulated composition of the wipers of the present invention may also comprise a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation that can contribute to excessive scaling or skin texture changes and against other environmental agents, which can cause skin damage.

A safe and effective amount of a chelating agent may be added to the encapsulated compositions of the subject invention, preferably from about 0.1% to about 10%, more preferably from about 1% to about 5%, by weight of the composition. Exemplary chelators that are useful herein are disclosed in U.S. Pat. No. 5,487,884 to Bissett et al.; U.S. Pat. No. 5,462,963 to Bush et al., and U.S. Pat. No. 5,364,617 to Bush et al. Preferred chelators useful in encapsulated compositions of the subject invention are furildioxime and derivatives thereof.

Flavonoids

The encapsulated composition of the wipers of the present invention may optionally comprise a flavonoid compound. Flavonoids are broadly disclosed in U.S. Pat. No. 5,686,082 to N'Guyen, U.S. Pat. No. 5,686,367 Hayashi, and U.S. Pat. No. 6,093,411 to Bissett. Favonoid compounds may be present in the encapsulated compositions at concentrations of from about 0.01% to about 20% by weight of the composition, more preferably from about 0.1% to about 10%, and most preferably from about 0.5% to about 5%.

Sterols

The encapsulated composition of the wipers of the present invention may comprise a safe and effective amount of one or more sterol compounds. Examples of useful sterol compounds include sitosterol, stigmasterol, campesterol, brassicasterol, lanosterol, 7-dehydrocholesterol, and mixtures thereof. These can be synthetic in origin or from natural sources, e.g., blends extracted from plant sources (e.g., phytosterols).

Anti-Cellulite Agents

The encapsulated composition of the wipers of the present invention may also comprise a safe and effective amount of an anti-cellulite agent. Suitable agents may include, but are not limited to, xanthine compounds (e.g., caffeine, theophylline, theobromine, and aminophylline).

Skin Lightening Agents

The encapsulated composition of the wipers of the present invention may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, ascorbic acid and derivatives thereof, e.g., magnesium ascorbyl phosphate or sodium ascorbyl phosphate or other salts of ascorbyl phosphate. Skin lightening agents suitable for use herein also include those described in U.S. Ser. No. 08/479,935 to Hillebrand, filed on Jun. 7, 1995; and U.S. Pat. No. 6,068,836 to Kvalnes et al.

Hydrophobic Conditioning Agents

The wipers of the present invention may comprise encapsulated compositions comprising one or more hydrophobic conditioning agents which are useful for providing a conditioning benefit to the skin and/or hair during the use of the wiper. The wipers of present invention may preferably comprise from about 0.5% to about 1,000%, more preferably from about 1% to about 200%, and most preferably from about 10% to about 100%, by weight of the substrate webs, of a hydrophobic conditioning agent.

The hydrophobic conditioning agent may be selected from one or more hydrophobic conditioning agents such that the weighted arithmetic mean solubility parameter of the hydrophobic conditioning agent is less than or equal to 10.5.

Nonlimiting examples of hydrophobic conditioning agents include those selected from the group consisting of mineral oil, petrolatum, lecithin, hydrogenated lecithin, lanolin, lanolin derivatives, $C_7$-$C_{40}$ branched chain hydrocarbons, $C_1$-$C_{30}$ alcohol esters of $C_1$-$C_{30}$ carboxylic acids, $C_1$-$C_{30}$ alcohol esters of $C_2$-$C_{30}$ dicarboxylic acids, monoglycerides of $C_1$-$C_{30}$ carboxylic acids, diglycerides of $C_1$-$C_{30}$ carboxylic acids, triglycerides of $C_1$-$C_{30}$ carboxylic acids, ethylene glycol monoesters of $C_1$-$C_{30}$ carboxylic acids, ethylene glycol diesters of $C_1$-$C_{30}$ carboxylic acids, propylene glycol monoesters of $C_1$-$C_{30}$ carboxylic acids, propylene glycol diesters of $C_1$-$C_{30}$ carboxylic acids, $C_1$-$C_{30}$ carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol $C_4$-$C_{20}$ alkyl ethers, di $C_8$-$C_{30}$ alkyl ethers, and combinations thereof.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the $C_7$-$C_{40}$ isoparaffins, which are $C_7$-$C_{40}$ branched hydrocarbons. Polydecene, a branched liquid hydrocarbon, is also useful herein and is commercially available under the trade names Puresyn 100® and Puresyn 3000® from Mobile Chemical (Edison, N.J.).

Also useful are various $C_1$-$C_{30}$ monoesters and polyesters of sugars and related materials. Suitable ester materials are further described in, U.S. Pat. No. 2,831,854 Tucker et al., U.S. Pat. No. 4,005,196 to Jandacek et al.; U.S. Pat. No. 4,005,195 to Jandacek; U.S. Pat. No. 5,306,516, to Letton et al.; U.S. Pat. No. 5,306,515 to Letton et al.; U.S. Pat. No. 5,305,514 to Letton et al.; U.S. Pat. No. 4,797,300 to Jandacek et al.; U.S. Pat. No. 3,963,699 to Rizzi et al,; U.S. Pat. No. 4,518,772 to Volpenhein; and U.S. Pat. No. 4,517,360 to Volpenhein.

Nonvolatile silicones such as polydialkylsiloxanes, polydiarylsiloxanes, and polyalkarylsiloxanes are also useful oils. These silicones are disclosed in U.S. Pat. No. 5,069,897 to Orr. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by GE Silicones, of Wilton, Conn. and the Dow Corning® 200 series sold by Dow Corning Corporation of Midland, Mich. Specific examples of polydimethylsiloxanes useful herein include Dow Corning® 225 fluid having a viscosity of 10 centistokes and a boiling point greater than 200 degrees C., and Dow Corning® 200 fluids having viscosities of 50, 350, and 12,500 centistokes, respectively, and boiling points greater than 200 degrees C. Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25 degrees C. being preferred. These materials are available, for example, as SF 1075 methylphenyl fluid (sold by General Electric Company) and 556 Cosmetic Grade phenyl trimethicone fluid (sold by Dow Corning Corporation). Alkylated silicones such as methyldecyl silicone and methyloctyl silicone are useful herein and are commercially available from General Electric Company. Also useful herein are alkyl modified siloxanes such as alkyl methicones and alkyl dimethicones wherein the alkyl chain contains 10 to 50 carbons. Such siloxanes are commercially available under the tradenames ABIL WAX 9810® ($C_{24}$-$C_{28}$ alkyl methicone) (sold by Goldschmidt) and SF1632 (cetearyl methicone)(sold by General Electric Company).

Vegetable oils and hydrogenated vegetable oils are also useful herein.

Also useful are $C_4$-$C_{20}$ alkyl ethers of polypropylene glycols, $C_1$-$C_{20}$ carboxylic acid esters of polypropylene glycols, and di-$C_8$-$C_{30}$ alkyl ethers. Nonlimiting examples of these materials include PPG-14 butyl ether, PPG-15 stearyl ether, dioctyl ether, dodecyl octyl ether, and mixtures thereof.

Hydrophilic Conditioning Agents

The encapsulated composition of the wipers of the present invention may optionally comprise one or more hydrophilic conditioning agents as therapeutic benefit agents. Nonlimiting examples of hydrophilic conditioning agents include those selected from the group consisting of polyhydric alcohols, polypropylene glycols, polyethylene glycols, ureas, pyrolidone carboxylic acids, ethoxylated and/or propoxylated $C_3$-$C_6$ diols and triols, alpha-hydroxy $C_2$-$C_6$ carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such as urea; guanidine; glycolic acid and glycolate salts (e.g., ammonium and quaternary alkyl ammonium); lactic acid and lactate salts (e.g., ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; cationic skin conditioning polymers (e.g., quaternary ammonium polymers such as Polyquaternium polymers); and mixtures thereof. Glycerol, in particular, is a preferred hydrophilic conditioning agent in the encapsulated composition of the wipers of the present invention. Also useful are materials such as aloe vera in any of its variety of forms (e.g., aloe vera gel), chitosan and chitosan derivatives, e.g., chitosan lactate, lactamide monoethanolamine; acetamide monoethanolamine; and mixtures thereof. Also useful are propoxylated glycerols as described in propoxylated glycerols described in U.S. Pat. No. 4,976,953 to Orr et al.

Preferred cleansing compositions that include therapeutic benefit agents are in the form of an emulsion, which further comprises an aqueous phase and an oil phase. As will be understood by the skilled artisan, a given component will distribute primarily into either the aqueous or oil phase, depending on the water solubility/dispersibility of the therapeutic benefit agent in the component. In one embodiment, the oil phase comprises one or more hydrophobic conditioning agents. In another embodiment, the aqueous phase comprises one or more hydrophilic conditioning agents.

Structured Conditioning Agents

The encapsulated therapeutic benefit agents of the wipers of the present invention may be structured conditioning agents. Suitable structured conditioning agents include, but are not limited to, vesicular structures such as ceramides, liposomes, and the like.

In another embodiment, the therapeutic benefit agents are comprised within a coacervate-forming composition. Preferably, the coacervate-forming composition comprises a cationic polymer, an anionic surfactant, and a dermatologically acceptable carrier for the polymer and surfactant.

Surface Cleaners

The encapsulated compositions may optionally contain effective amounts of surface cleaning agents such as quaternary compounds, proton donating antibacterial/cleaning agents, hydrophobic antibacterial/cleaning agents, chlorine stabilized cleaning agents, peroxide based cleaning agents, natural surfactant, and the like. Other such compositions as are known in the art for cleaning surfaces may also be likewise encapsulated.

Quaternary Compounds

Where the biocidal disinfecting material is a quaternary ammonium biocide, particularly useful quaternary ammonium germicides are those described in U.S. Pat. No. 6,268,327 to Lu et al. In this regard, quaternary ammonium biocides of this type have the nitrogen linked to four carbon-containing R groups and there is a salt-forming anionic member, such as a halide. The most preferred R groups are between 6 to 26 carbon atoms.

Particularly preferred exemplary quaternary ammonium salts which are quaternary ammonium biocides are alkyl ammonium halides such as cetyl trimethyl ammonium bromide, alkyl aryl ammonium halides such as alkyl dimethyl benzyl ammonium chloride, N-alkyl pyridinium halides such as N-cetyl pyridinium bromide, and the like. Other suitable types of quaternary ammonium salts may include those in which the molecule contains either amide or ester linkages such as octyl phenoxy ethoxy ethyl dimethyl benzyl ammonium chloride, N-(laurylcocoaminoformylmethyl)-pyridinium chloride, and the like. Other quaternary ammonium germicides are lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, and chlorinated dodecylbenzyltrimethyl ammonium chloride.

Examples of such preferred quaternary ammonium biocides are the BTC®, BARDAC®, and HYAMINE® biocides, such as BTC 2125M. BTC biocides are available from Stepan Co. (Northfield, Ill.), and BARDAC and HYAMINE biocides are available from Lonza, Inc (Allendale, N.J.).

May contain Polysiloxane quaternary ammonium salts as described in U.S. Pat. No. 5,854,147 to Nohr et al.

Proton Donating Antibacterial/Cleaning Agents

The encapsulated antimicrobial formulations of the wipers of the present invention comprise at least one proton donating agent along with one or more alkyl phosphate anionic surfactants. The one or more alkyl phosphate anionic surfactants are comprised, at least partially, of a mono alkyl phosphate. Although the proton donating agent may be an inorganic acid, it is generally a water soluble carboxylic acid having the following structure (I):

$$R-COOH \qquad (I)$$

wherein R may be lower alkyl, substituted lower alkyl, hydroxy lower alkyl, such as ($HOCH_2-$), carboxy lower alkyl, such as ($HOOC-CH_2CH_2-$), carboxy, hydroxy lower alkyl, such as ($HOOCCH_2CHOH-$), carboxy halo lower alkyl, such as ($HOOCCH_2CHBr-$), carboxy dihydroxy lower alkyl, such as ($HOOC-CHOH-CHOH-$), dicarboxy hydroxy lower alkyl, such as shown in structure (II):

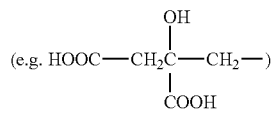

lower alkenyl, carboxy lower alkenyl, such as ($HOOCCH=CH-$), dicarboxy lower alkenyl, such as shown in structure (III)

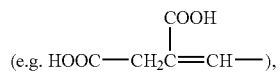

phenyl, such as $C_6H_5$, and substituted phenyl, such as hydroxy phenyl. As used herein, the term "lower" refers to an acid wherein R contains one to six carbon atoms. As used herein, the term "substituted" indicates that one or more hydrogen atoms are substituted by halogen atoms, hydroxyl groups, amino groups, thiol groups, nitro groups, cyano groups, etc.

More specifically, the following acids may be utilized in the encapsulated formulations of the wipers of the present invention: acetic acid, dehydroacetic acid, propionic acid, lactic acid, benzoic acid, parahydroxybenzoic acid, ascorbic acid, isoascorbic acid, citric acid, sorbic acid, formic acid, phosphoric acid, malic acid, tartaric acid, adipic acid, succinic acid, caprilic acid, glutaric acid, salicylic acid, boric acid, monohalogenacetic acid, dicarbonic acid, and fumaric acid. Also within the scope of the encapsulated compositions for use with the present invention are salts and esters of the acids described herein. Combinations and mixtures of the acids, acid esters, or acid salts described herein are also within the scope of the encapsulated compositions for use with the present invention. A preferred combination of acids for use in the encapsulated formulations used in the wipers of the present invention include malic acid and citric acid.

Hydrophobic Antibacterial/Cleaning Agents

It has been discovered that hydrophobic antimicrobial agents may be used in aqueous compositions to provide homogeneous antimicrobial compositions as the encapsulated composition for use in the wipers of the present invention. The encapsulated antimicrobial composition of the different aspects of the wipers of the present invention includes an effective amount of a hydrophobic antimicrobial agent which is at least partially dissolved in an amide and then combined with an aqueous mixture which may include a surfactant.

A wide range of hydrophobic antimicrobial agents which provide antimicrobial compositions may be used. The antimicrobial composition may include a single hydrophobic antimicrobial agent or a combination of two or more hydrophobic antimicrobial agents. Desirably, the hydrophobic antimicrobial agent may be a broad spectrum antimicrobial agent. For example, suitable hydrophobic antimicrobial agents include triclosan, triclocarban, and the like, and combinations thereof. Such hydrophobic antimicrobial agents are generally considered to be water insoluble by those skilled in the art. In a particular aspect, the antimicrobial composition includes triclosan to provide improved antimicrobial effectiveness. As used herein, the term "triclosan" refers to 2,4,4'-trichloro-2'-hydroxydiphenyl ether.

The hydrophobic antimicrobial agent may be present in the composition in any amount which provides an antimicrobial composition. However, if the amount of the hydrophobic antimicrobial agent is too high, the composition may be cloudy and irritating to the skin of the wearer. Moreover, if the amount of the hydrophobic antimicrobial agent is too low, the composition may not be antimicrobial. As set forth above, the antimicrobial effectiveness of the antimicrobial composition can be determined by testing the composition against several known microorganisms. It has been found that antimicrobial compositions which include from about 0.01 to about 3.0 weight percent, desirably from about 0.03 to about 1.0 weight percent and more desirably from about 0.05 to about 0.7 weight percent of the hydrophobic antimicrobial agent based on the total weight of the composition are effective against most microorganisms while not irritating the skin. It has also been found that the antimicrobial composition is particularly effective when it contains from about 0.01 to about 3.0 weight percent and more desirably from about 0.03 to about 1.0 weight percent triclosan based on the total weight of the composition.

The antimicrobial composition may also include other antimicrobial agents which may or may not be considered hydrophobic. For example, the antimicrobial composition may also include p-chloro-m-xylenol, benzalkonium chloride, chlorohexidine gluconate, hexachlorophene, and the like, and combinations thereof.

A wide range of amides which at least partially dissolve the hydrophobic antimicrobial agents may be used. For example, suitable amides include alkanolamides, long chain fatty acid diethanolamides, long chain fatty acid monoethanolamides, monoisopropanolamides, and the like, and combinations thereof. In a particular aspect, the amide includes at least about 50 weight percent and desirably at least about 90 weight percent of a lauric diethanolamide based on a total weight of the amide. It has been discovered that the use of a lauric diethanolamide is particularly desirable because of its solubility in water.

The amide may be present in the antimicrobial composition in any amount which provides the desired composition. However, if the amount of the amide is too high, the composition may be cloudy and irritating to the skin of the wearer. Moreover, if the amount of the amide is too low, the hydrophobic antimicrobial agent may not dissolve and the composition may not be homogeneous. It has been found that antimicrobial compositions which include from about 1.0 to about 15.0 weight percent, desirably from about 2.0 to about 10.0 weight percent, and more desirably from about 3.0 to about 5.0 weight percent of the amide based on the total weight of the composition are effective. It has also been found that the antimicrobial composition is particularly effective when it contains from about 2.0 to about 10.0 and more desirably from about 3.0 to about 5.0 weight percent of an alkanolamide based on the total weight of the composition.

A wide range of surfactants may also be used in the encapsulated compositions used in the wipers of the present invention. It has been hypothesized that the surfactant acts to prevent the precipitation of the active mixture of the hydrophobic antimicrobial agent and amide in the water. Suitable surfactants include those which prevent such precipitation. For example, suitable surfactants may include anionic surfactants, nonionic surfactants, cationic surfactants, amphoteric surfactants and combinations thereof as are well known to those skilled in the art. Suitable anionic surfactants include sodium laureth sulfate, sodium-lauryl methyl taurate, myristoyl sarcosine, sodium dodecylbenzene sulfonate, and the like.

Suitable nonionic surfactants include the polyoxyethylene ethers of the higher fatty alcohols and alkyl phenols; the polyethylene glycols of fatty acids; fatty alkylol amide condensation products; polymers of ethylene and propylene oxides; compounds formed by the addition of propylene oxide to ethylene diamide, followed by the addition of ethylene oxide; fatty acid ethylene oxide condensation products; ethoxylate carboxylic acid; ethoxylate glycerides; and glycol esters. In a particular aspect, the surfactant is desirably a nonionic surfactant, such as octoxynol-9, which provides an improved composition because of it's solubility in water and low level of irritation to the skin.

The surfactant may be present in the antimicrobial composition in any amount which provides the desired composition. However, if the amount of the surfactant is too high, the composition may be cloudy and cause excessive foaming. Moreover, if the amount of the surfactant is too low, the active mixture may precipitate and composition may not be clear and homogeneous. The encapsulated antimicrobial which include from about 1.0 to about 30.0 weight percent, desirably from about 1.0 to about 20.0 weight percent and more desirably from about 4.0 to about 10 weight percent of the surfactant based on the total weight of the composition are effective. If it is desired to use the antimicrobial composition in a wet wipe or similar product, the amount of surfactant should not cause excessive foaming of the composition. For example, encapsulated antimicrobial compositions which include less than about 10.0 weight percent and desirably less than about 7.0 weight percent of the surfactant based on the total weight of the composition have been found to be particularly effective with wet wipes.

The antimicrobial compositions may also include additional elements such as, for example, emollients, perfuming agents, chelating agents, cleansing agents, foam stabilizers, preservatives, protectants, and the like, to enhance the performance of the compositions.

Accordingly, the different aspects of the encapsulated compositions of the wipers of the present invention may provide antimicrobial compositions which include hydrophobic antimicrobial agents in an aqueous environment. In a particular aspect, the composition defines an MIC value of 100 ppm (parts per million active) or less against *E. coli* (ATCC #11229) and *S. aureus* (ATCC #6538) (both bacteria), and an MIC value of 10,000 ppm or less against *C. albicans* (ATCC #10231) (yeast), desirably defines an MIC value of 10 ppm or less against *E. coli* (ATCC #11229) and *S. aureus* (ATCC #6538) (both bacteria), and an MIC value of 1,000 ppm or less against *C. albicans* (ATCC #10231) (yeast), and more desirably defines an MIC value of 1 ppm or less against *E. coli* (ATCC #11229) and *S. aureus* (ATCC #6538) (both bacteria), and an MIC value of 1,000 ppm or less against *C. albicans* (ATCC #10231) (yeast). Such aqueous, antimicrobial compositions are particularly useful in premoistened wipes and cosmetic products such as liquid soaps, shampoos, and lotions.

The antimicrobial composition may be prepared by a method which involves combining an active mixture of the hydrophobic antimicrobial agent and the amide with a mixture of the surfactant and water. The homogeneous antimicrobial composition may include an effective amount of a hydrophobic antimicrobial agent which is dissolved in an amide to form an active mixture which is then combined with a surfactant/water mixture to provide the antimicrobial composition.

Chlorine Stabilized Cleaning Agents

Chlorine stabilizing agents are well known and include, for example, sulfamic acid and water soluble salts thereof, alkyl sulfamates, cycloalkyl sulfamates, aryl sulfamates, alkyl sulfonamides and aryl sulfonamides. Sulfamic acid and water soluble salts thereof are particularly preferred. Such water soluble salts include, for example, sodium, potassium, magnesium, calcium, lithium and aluminum salts of sulfamic acid. Other particularly preferred chlorine stabilizing agents include, for example, benzene sulfonamide, toluene sulfonamide and 4-carboxybenzene sulfonamide melamine. Sulfamic acid itself, however, is most preferred.

Peroxide Based Cleaning Agents

Peroxides such as hydrogen peroxide, sodium carbonate-hydrogen peroxide adduct, and sodium perborate have been conventionally used together with N-acyl compounds such as tetraacetylethylenediamine (TAED), tetraacetylglycoluryl (TAGU), and esters such as glucose pentaacetate and saccharose octaacetate, to improve the bleaching power. Various nitrile compounds have been also proposed as a bleach activating agent for improving the bleaching power of the peroxides. For example, various nitrites have been proposed as a useful bleach activating agent in United Kingdom Patent No. 802,035, iminodiacetonitrile has been proposed as a useful bleach activating agent in U.S. Pat. No. 3,882,035 to Loffelman et al., and p-chlorobenzoyl cyanamide has been proposed as a useful bleach activating agent in Japanese Patent Application Laid-Open No. 52-52880.

Natural Surfactants

Cleaning compositions may include sodium myreth sulphate (a coconut based surfactant) and their respective formulations and naturally antiseptic Birch Bark Extract to boost cleaning efficacy.

Natural surfactants from emulsions formed of a hydrocarbon bitumen, ideally bitumen such as Cerro Negro bitumen. (As described in U.S. Pat. No. 5,792,223 to Rivas et al., Natural surfactant with amines and ethoxylated)

Cleaning solvents made from corn, soybeans. For example those manufactured by NTEC Versol, Inc (Mt. Prospect, Ill.) and described in U.S. Pat. No. 6,096,699 to Bergemann et al.

EXAMPLES

The invention is further described with reference to the following detailed examples, which illustrate several compositions that may be encapsulated and sandwiched between various substrate webs to form various embodiments of the wipers of the present invention. The examples are included for illustrative purposes and should not be construed as limiting the invention.

Example 1

An aqueous antibacterial liquid cleansing formulation may be encapsulated in a LDPE pouch. The amount of formulation may vary depending on the size of the substrate chosen. Said formulation may be diluted with water or other suitable diluents (in some cases alcohol, and other solvents but no way limited by them). The composition ratio of the formulation and water (or diluent) may be in the ratio of 1:99 to 99:1 by weight or volume. Further, the amount of water (or diluent) so chosen is in the range of 1 to 500% saturation of the wiper in which the capsule is placed.

An exemplary aqueous antimicrobial liquid cleansing formulation is described in U.S. Pat. No. 5,837,274 to Shick et al. and is given below:

| INGREDIENT | Percent Composition (Broad Range) | Percent Composition (Narrower Range) |
| --- | --- | --- |
| WATER PHASE | | |
| Deionized water | 20.0 to 75.0 | 25.0 to 35.0 |
| Ucare JR 400 | 0.05 to 0.5 | 0.1 to 0.25 |
| SURFACTANT PHASE | | |
| Miracare MS-1 | 20.0 to 50.0 | 40.0 to 50.0 |
| Standamox CAW | 2.0 to 10.0 | 4.0 to 6.0 |
| Topicare PP-15 | 0.5 to 5.0 | 1.0 to 3.0 |
| Amercil 357 | 0.0 to 1.0 | 0.0 to 1.0 |
| PRESERVATIVE PHASE | | |
| Glycerine | 1.0 to 10.0 | 5.0 to 10.0 |
| DMDM Hydantoin | 0.4 or as needed | 0.4 or as needed |
| Tetrasodium EDTA | 0.1 or as needed | 0.1 or as needed |
| ACTIVE PHASE | | |
| Triclosan | 0.1 to 1.0 | 0.5 to 1.0 |
| Tween 40 | 1.0 to 5.0 | 1.0 to 3.0 |
| Fragrance | 0.0 to 0.3 | 0.0 to 0.1 |

Approximately 5 ml of the above formulation was mixed with 20 ml of water and thoroughly mixed. The 25 ml of solution was poured into a LDPE pouch measuring 2 inches (51 mm)×3.5 inches (89 mm) and thermal sealed at the edges of the pouch. Failure points were created along the edges by excessive thermal sealing. The pouch was then placed between two substrate webs of a high pulp content hydraulically entangled nonwoven composite fabric, made by the process of U.S. Pat. No. 5,284,703 to Everhart et al. and available from Kimberly-Clark Corporation, Roswell, Ga., under the name HYDROKNIT®. Each substrate web had a basis weight of approximately 128 g/m$^2$ and a size of 12 inches (305 mm)×12 inches (305 mm). The substrate webs were adhered to each other, with the pouch sandwiched between them, using a hot melt adhesive such as commercially available from Ashland Specialty Chemical, Dublin, Ohio under the tradename AROMELT®.

With the edges tucked in to create easy holding and twisting at the ends of the rolled product. Upon twisting, the wiper was partially saturated with the cleansing solution and used to wipe dirty hands.

Further, the pouches may alternatively be created as to incorporate a weak spot for rupture or failure upon the exertion of pressure. These failure points may be created by varying the thickness of the pouch material (in this case the LDPE pouch) for example by thermal scrapping of the layers to reduce wall thickness.

Example 2

A cleansing wiper may be made of two substrate webs of 1.0 oz/yd$^2$ (33.9 g/m$^2$) polypropylene spunbond material, each measuring approximately 9 inches (229 mm) by 9 inches (229 mm). The wiper may have a 70% loading, by weight of the substrate webs, of wax micro-capsules containing a cleansing formulation.

The spherical micro-capsules may be approximately 1 mm in diameter. Each micro-capsule may contain approximately 1 mL of the cleansing formulation. Such wax micro-capsules may be made of a commercially available pressure-sensitive microcrystalline wax, such as MULTIWAX® W-445 from Chemtura Corporation, Middlebury, Conn.

Such wax microcapsules may contain an aqueous cleanser formulation such as described in U.S. Pat. No. 5,910,455 to Maddern et al. and given below:

| | % by weight |
| --- | --- |
| Blend of paramenthadienes (TABS DS terpene mixture) | 7.00 |
| PPG-2 Methyl Ether | 4.00 |
| PPG-1-PEG-9 Lauryl Glycol Ether | 6.00 |
| PEG-40 Hydrogenated Castor Oil | 6.00 |
| Phenoxyethanol | 0.16 |
| Methyldibromo Glutaronitrile | 0.04 |
| Aloe Barbadensis Gel | 0.01 |
| Parfum (Orange citrus fragrance) | 1.40 |
| Aqua (water) | 75.39 |

The micro-capsules may be placed between the substrate webs and substrate webs may be bonded to each other by ultrasonic bonding on the edges and across the center of the wiper 10. The molten wax would act as an adhesive to the substrate during deposition. This embodiment would be activated by application of pressure to the wiper 10, rupturing the wax beads and releasing the cleansing formulation.

Example 3

An antibacterial wipe may be made of two substrate webs of HYDROKNIT® material each having a basis weight of 128 g/m$^2$, manufactured by Kimberly-Clark Corporation. The size of the wiper may be 10 inches (254 mm)×10 inches (254 mm). The wiper may have a 400% loading; by weight of the substrate webs, of polyethylene pouches containing an antibacterial formulation.

Each of the pouches may be approximately 1 cm×1 cm. The pouches may be placed between the substrate web and the substrate webs may be thermally bonded to each other on the edges. The pouch can be made from poly-coated kraft paper, having a 10# gloss poly coating on one side and 50# virgin kraft paper on the other. Such FDA approved laminates are commercially available from PackagingPrice.com, Inc., Barrington, Ill. (Stock # KPPC1850). The pouch may be thermal sealed along the edges and could be pressure triggered. Such pouches may have a pressure and water trigger.

An example of an aqueous antibacterial formulation that may be encapsulated in each of the pouches is described in U.S. Pat. No. 6,228,385 to Shick, and is given below:

| INGREDIENT | Percent Composition (Broad Range) | Percent Composition (Narrower Range) |
| --- | --- | --- |
| HUMECTANT | | |
| Glycerin | 1.0 to 15.0 | 1.0 to 5.0 |
| PARTICULATE DELIVERY MATERIAL | | |
| Acrylates Copolymers | 0.1 to 5.0 | 1.0 to 2.5 |
| EMOLLIENT % loading in particulate delivery material | | |
| Dimethicone | 10 to 80 | 40 to 70 |
| AQUEOUS ALCOHOLIC BASE | to make up 100% | to make up 100% |
| Water | 1 to 78.5 | 1 to 38.5 |
| Ethanol | 20 to 90 | 60 to 80 |
| OTHER INGREDIENTS | | |
| Carbomer ® | 940 0.0 to 1.0 | 0.0 to 0.5 |
| Triethanolamine | 0.0 to 1.0 | 0.0 to 0.5 |
| Klucel ® 99-HHF hydroxylpropyl cellulose | 0.0 to 1.0 | 0.0 to 0.5 |
| Fragrance | 0.0 to 1.0 | 0.0 to 0.5 |

Example 4

A polypropylene melt blown substrate, such as described in U.S. Pat. No. 4,100,324; U.S. Pat. No. 4,604,313 or U.S. Pat. No. 4,820,577, having a basis weight of approximately 50 g/m², and measuring 9 inches (229 mm) by 9 inches (229 mm) could be used for a scrubbing hand cleanser wiper. The wiper could incorporate a cleaning formulation encapsulated in wax micro-capsules measuring approximately 2 mm in diameter. The wax micro-capsules may be made of a commercially available pressure-sensitive microcrystalline wax, such as MULTIWAX® W-445 from Chemtura Corporation, Middlebury, Conn.

The cleansing formulation may also include silica grit particles, which would act like micro scrubbers for easy removal of grease during the act of cleansing. Such grit may have a sieve size ranging from 3 to 200 USS (United States Standard Sieve) or a micro grit size of 240 to 600 USS. The formulation would constitute 70% by weight of the webs; the silica grit (size 240) would constitute 20% by weight of the webs, the wax wall 10% by weight of the webs. The silica grit may be incorporated either in the cleaning formulation or in the wax itself.

An example of an aqueous cleanser formulation that may be used is described in U.S. Pat. No. 6,432,429 to Maddern et al. and is given below:

| | % by weight |
| --- | --- |
| Octyl Cocoate | 3.0 |
| Propylene glycol | 3.0 |
| C11-15 Pareth-5 | 3.0 |
| Sodium Pyrrolidone Carboxylate (50% by weight aqueous solution) | 1.0 |
| Sodium Laureth-11 Carboxylate (22% by weight aqueous solution) | 2.5 |
| Methylparaben | 0.1 |
| Propylparaben | 0.1 |
| Quaternium-15 | 0.2 |
| Water | up to 100 |

An alternate aqueous cleanser formulation that may be encapsulated and incorporated into the wiper as described is also described in U.S. Pat. No. 6,432,429 to Maddern et al. and is given below:

| | % by weight |
| --- | --- |
| PPG-1n-Propyl Ether | 4.0 |
| D-Limonene (Dipentene) | 7.0 |
| Alcohol ethoxylate (OE 7) | 4.0 |
| PEG-200 Hydrogenated Glyceryl Palmitate and PEG-7 Glyceryl Cocoate (blend) | 3.0 |
| Methyl Paraben | 0.2 |
| Propyl Paraben | 0.1 |
| Quaternium 15 | 0.1 |
| Tocopheryl acetate | 0.1 |
| B.H.A | 0.02 |
| Water | up to 100 |

Example 5

A cloth-like nonwoven webs 10 inches (254 mm)×10 inches (254 mm) made from thermoplastic polymers such as described in U.S. Pat. No. 6,797,377 to DeLucia, could be used as substrate for a disposable wash cloth application. Pouches measuring 1.0 inch (25 mm)×2.0 inches (51 mm) and made of Poly Vinyl Alcohol (PVOH) 51-05 sheet, like the one from E.I. DuPont de Nemours & Company (Wilmington, Del.) and sold under the brand name Elvanol®, may be placed between the nonwoven webs. Depending on the amount of water resistance needed, the PVOH may be cross-linked using an insolubilizer. Examples of insolubilizers are salts of multivalent ions (i.e., ammonium zirconium carbonates), aminoplast resins (i.e., cyclic amide condensates), and aldehyde or aldehyde derivatives. Such a pouch may be triggered by water, pressure or increased temperature.

The pouches encapsulating the cleansing formulation may be adhesively bonded to the substrate at or near the edge. A poly vinyl acetate (PVA) adhesive, such as the commercially available 3M™ Super 77™ Spray Adhesive from 3M, St. Paul, Minn., may be used to adhere the pouch to the substrate web and to bond substrate webs together to form the wiper. The wiper may then be rolled up into a rolled form, such as shown in FIG. 4A, for protection of the pouch and ease in packaging, storing and transporting.

An example of a cleansing formulation that may be encapsulated in the exemplary pouches of the wiper may be as described in U.S. Pat. No. 6,806,213 to Brooks, and as given below:

| Class | Compound | Percent (%) |
| --- | --- | --- |
| Deionized water | | 96.9975 |
| Solubilizing agent | Propylene glycol | 1.5 |
| Preservative | GLYDANT PLUS | 0.3 |
| Mild surfactant | MACKAM 2C | 0.5 |
| Moisturizer | Glycerin | 0.4 |
| Skin vitamin | MIRACARE SML E/5 | 0.01 |
| Aloe | Aloe | 0.0025 |
| Fragrance | Fragrance | 0.06 |
| Solubilizing agent | Polysorbate 20 | 0.23 |

An alternate aqueous cleanser formulation that may be encapsulated and incorporated into the wiper as described is also described U.S. Pat. No. 6,806,213 to Brooks and is given below:

| Class | Compound | Percent (%) |
| --- | --- | --- |
| Deionized water | | 98.0475 |
| Preservative | MACKSTAT H-66 | 0.6 |
| Preservative | Disodium EDTA | 0.15 |
| Mild surfactant | MACKAM 2C | 0.5 |
| Moisturizer | Glycerin | 0.4 |
| Skin vitamin | MIRACARE SML E/5 | 0.01 |
| Aloe | Aloe | 0.0025 |
| Fragrance | Fragrance | 0.06 |
| Solubilizing agent | Polysorbate 20 | 0.23 |

Example 6

A surface sanitizing wipe measuring 8 inches (203 mm)×8 inches (203 mm) may be made of webs abrasion resistant fibrous nonwoven composite such as described in U.S. Pat. No. 5,350,624 to Georger et al. The wiper may have a 250% loading, by weight of the substrate webs, of wax micro-capsules containing a cleansing formulation.

The spherical micro-capsules may be approximately 3 mm in diameter. Each micro-capsule may contain approximately 3 mL of the cleansing formulation. The wax micro-capsules may be made of a commercially available pressure-sensitive microcrystalline wax, such as MULTIWAX® W445 from Chemtura Corporation, Middlebury, Conn. The micro-capsules may be placed at a central location between the substrate webs and substrate webs may be bonded to each other by ultrasonic bonding on the edges and across the center of the wiper.

The surface sanitizing formulation may be the same formulation as used in the commercially available KIMTECH PREP® Surface Sanitizer Wipes, from Kimberly-Clark Corporation, Roswell, Ga., and as described below:

| | |
| --- | --- |
| Octyl decyl dimethyl ammonium chloride | 0.0120% |
| Dioctyl dimethyl ammonium chloride | 0.0048% |
| Didecyl dimethyl ammonium chloride | 0.0072% |
| Alkyl (C14, 50%; C12, 40%; C16, 10%) dimethyl benzyl ammonium chloride | 0.016% |
| Inert ingredients | 99.9600% |

Example 7

The same substrate webs and micro-capsules as discussed in Example 6 may also be used to encapsulate a sunscreen formulation. An example of a sunscreen formulation that may be used is described in U.S. Pat. Publication 2004/0228811 to Krzysik, filed May 13, 2003, and is given below:

| Ingredient | Weight % (Based on Total Formulation Weight) |
| --- | --- |
| WATER PHASE | |
| Water | 64.75 |
| Glycerin | 5.0 |
| Triethanolamine | 0.1 |
| Methyl Paraben | 0.15 |
| DMDM Hydatoin | 1.0 |
| OIL PHASE | |
| C12-C15 Alkyl Benzoate | 3.0 |
| Butyl Methoxydibenzoylmethane | 3.0 |
| Octyl Methoxycinnamate | 7.5 |
| Mentyl Anthranilate | 5.0 |
| Octyl Salicylate | 5.0 |
| Sorbitan Monoleate | 0.1 |
| Dow Corning 245 Fluid | 5.0 |
| Pina Colada II | 0.25 |
| Pemulen TR-2 | 0.15 |

Example 8

The same substrate webs and pouches as discussed in Example 3 may also be used to encapsulate a skin health formulation. An example of one embodiment would be a formulation having skin health benefits as described in U.S. Pat. No. 6,440,437 to Krzysik et al. and as given below:

| | weight percent |
| --- | --- |
| Water | qs to 100% |
| Glycerin | 5% |
| Glyceryl stearate SE | 3% |
| Borage oil | 1% |
| Aloe | 0.3% |
| Tocopherol acetate | 0.3% |

Suitable pH adjuster to pH 5.5

An alternative example of another formulation having skin health benefits that could be used is also described in U.S. Pat. No. 6,440,437 to Krzysik et al. and is given below:

| | weight percent |
| --- | --- |
| Water | qs to 100% |
| Glycerin | 3.3% |
| Glyceryl stearate SE | 1.98% |
| Borage oil | 0.66% |
| Soy sterol | 0.53% |
| PROLIPID 141 (International Specialty Products, Wayne, NJ) | 0.66% |
| Aloe | 0.2% |
| Tocopherol acetate | 0.2% |

Suitable pH adjuster to pH 5.5

While the invention has been described in conjunction with several specific embodiments, it is to be understood that many alternatives, modifications, and variations will be apparent to those skilled in the art in light of the foregoing description. Accordingly, this invention is intended to embrace all such alternatives, modifications, and variations that fall within the spirit and the scope of the appended claims.

We claim:

1. A substantially dry wiper comprising:
   a substantially dry first substrate web and a substantially dry second substrate web, the first and second substrate webs being joined to one another in a face-to-face configuration; and
   a plurality of primary capsules, wherein each primary capsule is disposed between the first substrate web and the second substrate web and encapsulates a primary agent,
   where the primary agent is released from the primary capsules to the first and second substrate webs upon the occurrence of a primary triggering event.

2. The wiper of claim 1, where the first substrate web is a nonwoven web.

3. The wiper of claim 1, where the first substrate web contains cellulose fibers.

4. The wiper of claim 1, where the first substrate web is the same materials as the second substrate web.

5. The wiper of claim 1, where the first substrate web is a different material than the second substrate web.

6. The wiper of claim 1, wherein the plurality of primary capsules comprises a plurality of primary microcapsules disposed between the first substrate web and the second substrate web forming a layer of primary microcapsules over a distinct area of the wiper, and where the primary microcapsules contain the primary agent.

7. The wiper of claim 1, where the primary agent is selected from the group containing: water, cleaning solution, soap, degreaser, disinfectant, sanitizer, antibacterial substance, moisturizer, emollient, medicine, pH buffer, indicator, cosmetic, or beauty care substance.

8. The wiper of claim 1, where the primary triggering event is selected from the group containing: applied pressure, atmospheric pressure, temperature, moisture, pH, or contact with a specific substance.

9. The wiper of claim 1, where the primary triggering event is contact with water, urea, alcohol, an organic solvent, an acid, a base, or other specific liquid.

10. The wiper of claim 1, where the primary triggering event is the rolling of the wiper and twisting the opposite ends of the rolled wiper in opposite rotational directions in relation to each other.

11. A substantially dry wiper comprising:
    a substantially dry first substrate web and a substantially dry second substrate web, the first and second substrate webs being joined to one another in a face-to-face configuration; and
    at least one primary capsule, where the primary capsule is disposed between the first substrate web and the second substrate web and encapsulates a primary agent,
    at least one secondary capsule where the secondary capsule is disposed between the first substrate web and the second substrate web and contains a secondary agent, the secondary agent being different than the primary agent,
    where the primary agent is released from the primary capsule to the first and second substrate webs upon the occurrence of a primary triggering event and
    where the secondary agent is released from the secondary capsule to the first substrate web and the second substrate web upon the occurrence of a secondary triggering event.

12. The wiper of claim 11, wherein the at least one secondary capsule comprises a plurality of secondary microcapsules disposed between the first substrate web and the second substrate web forming a layer of secondary microcapsules over a distinct area of the wiper, and where the secondary microcapsules contain the secondary agent.

13. The wiper of claim 11, where the primary triggering event is the same as the secondary triggering event.

14. The wiper of claim 11, where the primary triggering event is different than the secondary triggering event.

15. The wiper of claim 11, where the secondary triggering event is contact with the primary agent.

16. A method for cleaning a surface with a substantially dry wiper comprising
    a. providing a wiper having a substantially dry first substrate web and a substantially dry second substrate web joined together in a face-to face configuration and a plurality of primary capsules disposed between the first and second substrate webs, the primary capsules containing a primary agent;
    b. exposing the primary capsules to a primary triggering event that releases the primary agent from the primary capsules to the first and second substrate webs; and
    c. cleaning the surface with the wiper.

17. The method of claim 16, wherein the plurality of primary capsules comprises a plurality of primary microcapsules disposed between the first and second substrate webs, where the primary microcapsules contain the primary agent.

18. The method claim 16, where the wiper further comprises at least one secondary capsule disposed between the first and second substrate webs and the at least one secondary capsule contains a secondary agent, where the secondary agent is different than the primary agent, and where the secondary agent is released from the secondary capsule upon exposure to a secondary triggering event.

19. The method of claim 18, where the secondary triggering event is different than the primary triggering event.

20. The method of claim 16, further comprising the step of rolling the provided wiper prior to exposure to the primary triggering event, and where the primary triggering event is the twisting of the opposite ends of the rolled wiper in opposite rotational direction relative to each other.

* * * * *

UNITED STATES PATENT AND TRADEMARK OFFICE
CERTIFICATE OF CORRECTION

PATENT NO. : 7,614,812 B2  Page 1 of 1
APPLICATION NO. : 11/238923
DATED : November 10, 2009
INVENTOR(S) : Reddy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 674 days.

Signed and Sealed this

Nineteenth Day of October, 2010

David J. Kappos
*Director of the United States Patent and Trademark Office*